United States Patent
Jacobs, Jr. et al.

(10) Patent No.: US 8,591,918 B2
(45) Date of Patent: Nov. 26, 2013

(54) MYCOBACTERIAL MUTANTS INDUCING IL-12

(75) Inventors: William R. Jacobs, Jr., Pelham, NY (US); Kari Sweeney, Stamford, CT (US); Dee Dao, Bronx, NY (US); Steven A. Porcelli, Bronx, NY (US); John Chan, Hastings-on-Hudson, NY (US); Tsungda Hsu, New York, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 342 days.

(21) Appl. No.: 12/450,193

(22) PCT Filed: Mar. 10, 2008

(86) PCT No.: PCT/US2008/003204
§ 371 (c)(1),
(2), (4) Date: Sep. 8, 2011

(87) PCT Pub. No.: WO2009/008912
PCT Pub. Date: Jan. 15, 2009

(65) Prior Publication Data
US 2012/0141533 A1  Jun. 7, 2012

Related U.S. Application Data

(60) Provisional application No. 60/918,997, filed on Mar. 19, 2007, provisional application No. 60/930,839, filed on May 17, 2007.

(51) Int. Cl.
*A61K 39/04* (2006.01)
*A61K 49/00* (2006.01)
*A01N 63/00* (2006.01)

(52) U.S. Cl.
USPC ......... 424/248.1; 424/9.1; 424/9.2; 424/93.1; 424/93.2

(58) Field of Classification Search
USPC .............. 424/9.1, 9.2, 93.1, 93.2, 248.1
See application file for complete search history.

(56) References Cited

U.S. PATENT DOCUMENTS

| | | | |
|---|---|---|---|
| 6,372,478 B1 | 4/2002 | Bloom | |
| 6,733,761 B2 | 5/2004 | McKinney | |
| 6,752,994 B2 | 6/2004 | Jacobs, Jr. | |
| 6,821,769 B2 | 11/2004 | Alland | |
| 7,722,861 B2 | 5/2010 | Jacobs | |
| 7,758,874 B2 | 7/2010 | Jacobs, Jr. | |
| 7,939,089 B2 | 5/2011 | Jacobs | |
| 7,998,471 B2 | 8/2011 | Jacobs, Jr. | |
| 2003/0147861 A1 | 8/2003 | Watson et al. | |
| 2007/0009547 A1 | 1/2007 | Brosch et al. | |
| 2007/0202131 A1 | 8/2007 | Jacobs, Jr. | |
| 2009/0110696 A1 | 4/2009 | Jacobs, Jr. | |
| 2010/0297185 A1 | 11/2010 | Jacobs, Jr. | |

FOREIGN PATENT DOCUMENTS

WO   WO 2006/076518 A2   7/2006

OTHER PUBLICATIONS

International Search Report for PCT Application No. PCT/US2008/003204, 2009.
Written Opinion of the International Searching Authority for PCT Application No. PCT/US2008/003204, 2009.
Van Pittius et al. "The ESAT-6 gene cluster of *Mycobacterium tuberculosis* and oher high G+C gram-positive bacteria." Genome Biology, 2001, 2:10, pp. 1-18.
*Mycobacterium smegmatis* str. MC2 155, complete genome. NCBI Reference Sequence pp. 125-127. Retrieved from the NCBI Sequence Database, 2009.
Yuan et al. "A common mechanism for the biosynthesis of methoxy and cyclopropyl mycolic acids in *Mycobacterium tuberculosis*." Proc. Nat. Acad. Sci. USA, 93:23,12828-12833, 1996.
Indigo et al. "Cord factor trehalose 6,6'-dimycolate (TDM) mediates trafficking events during mycobacterial infection of murine macrophases." Microbio. 2003, 2049-2059.
Salman et al. "Synthesis of mycolic acids of mycobacteria: an assessment of the cell-free system in light of the whole genome." Biochi. et Biophys. Acta 1437, 1999, 325-332.

*Primary Examiner* — Rodney P. Swartz
(74) *Attorney, Agent, or Firm* — Amster, Rothstein & Ebenstein LLP

(57) ABSTRACT

Provided are mycobacteria deleted in at least a portion of a region 3 ESAT-6-like gene cluster. Also provided are mycobacteria comprising a mutation in an roc-1 gene. Additionally, vaccines comprising these mycobacteria are provided. Further provided are methods of making a recombinant *mycobacterium*, methods of inducing an immune response in a mammal, methods of inhibiting IL-12 production in a mammal, and methods of stimulating IL-12 production in a mammal. Vaccine adjuvants are also provided, as are methods of inducing immunity to a target antigen in a mammal.

25 Claims, 21 Drawing Sheets

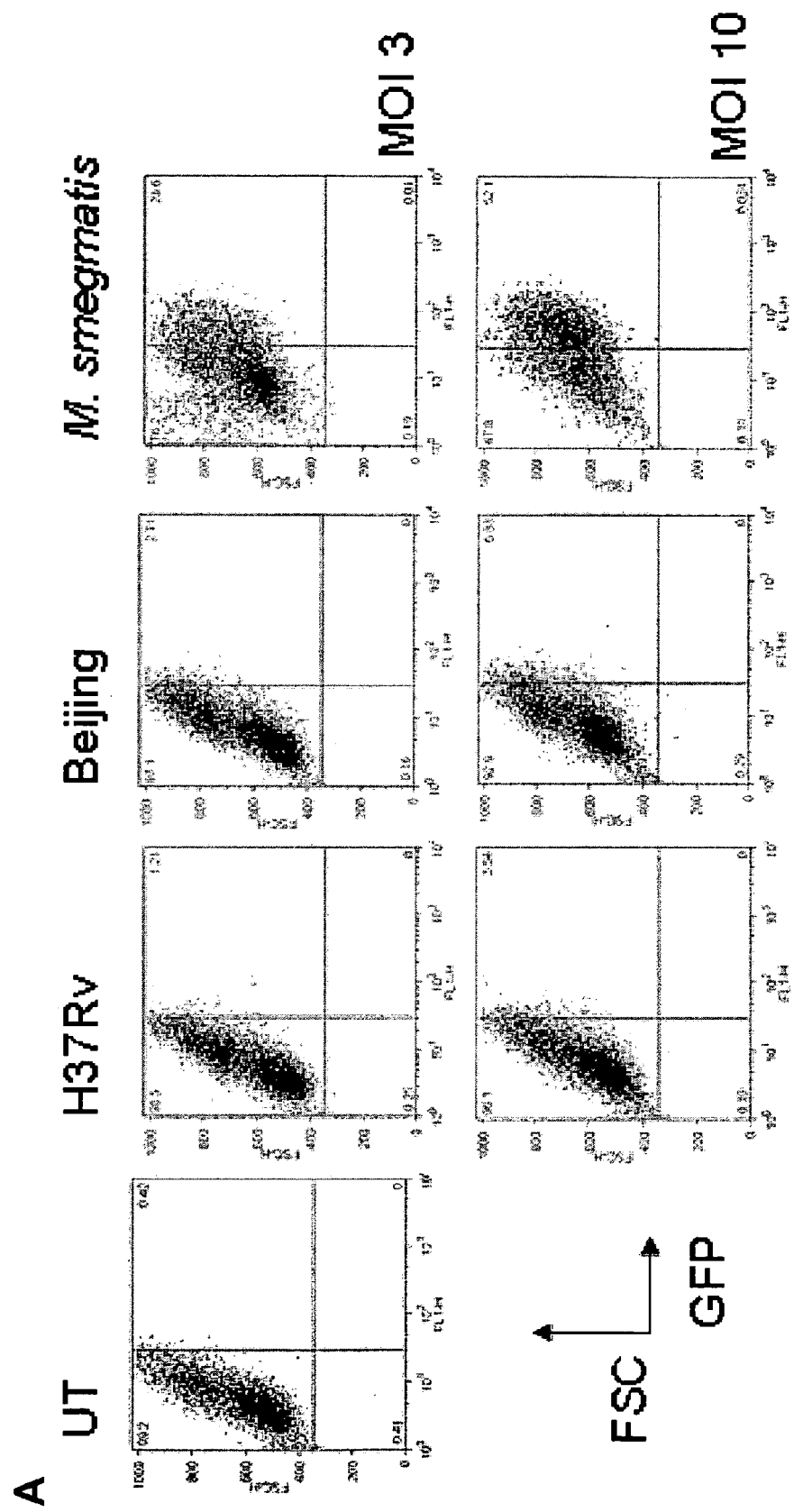

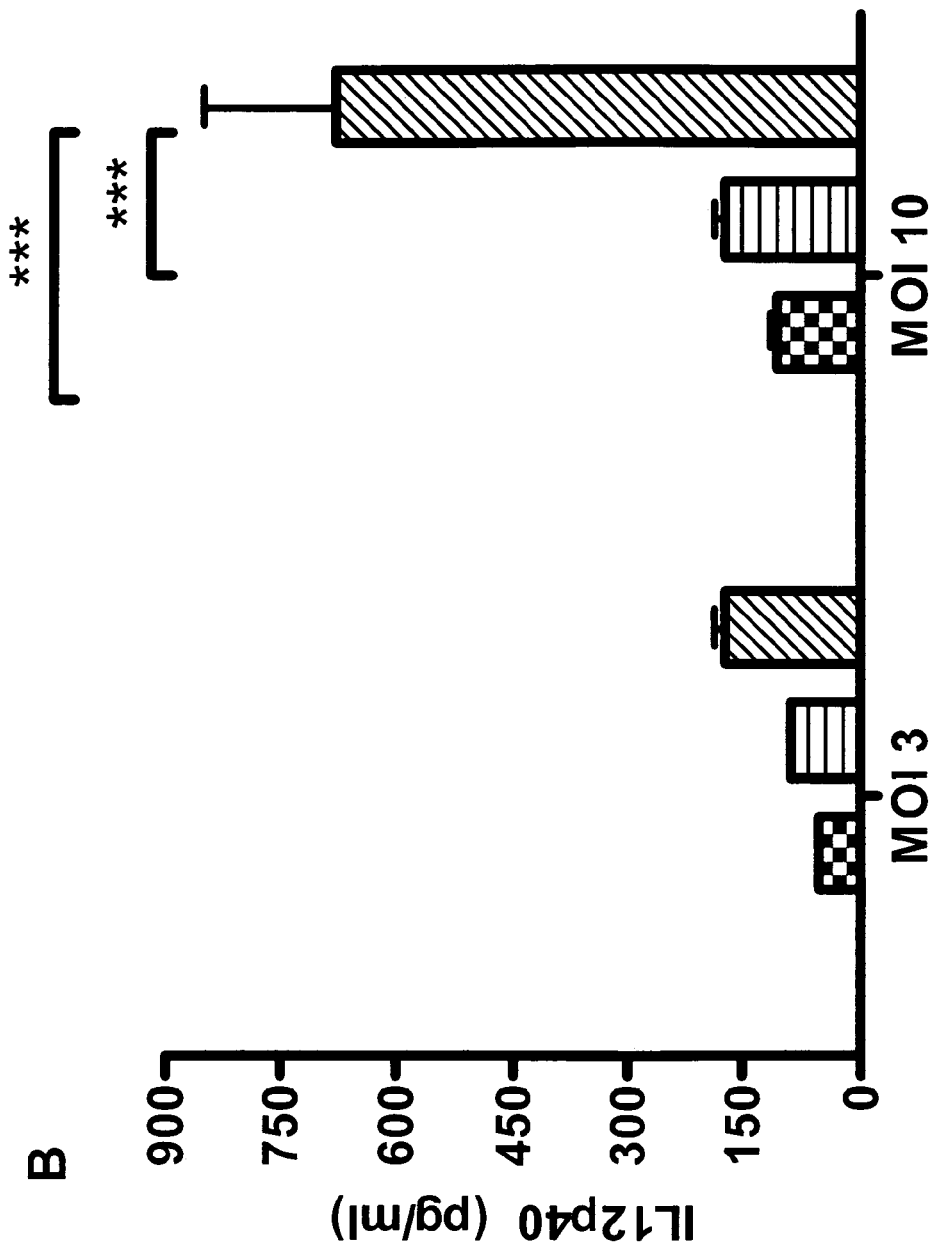

FIG. 3(A-B)
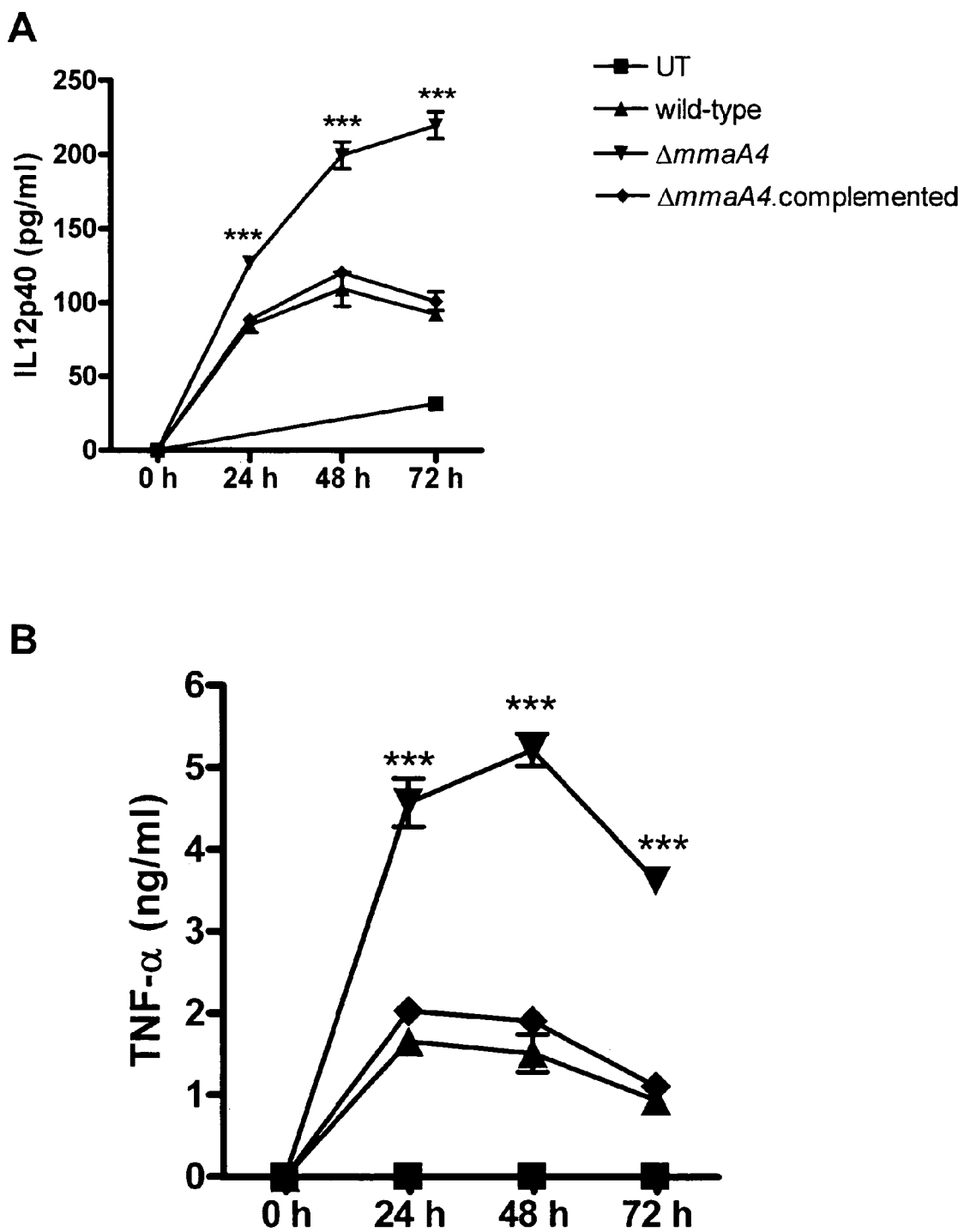

FIG. 4(A-B)
A
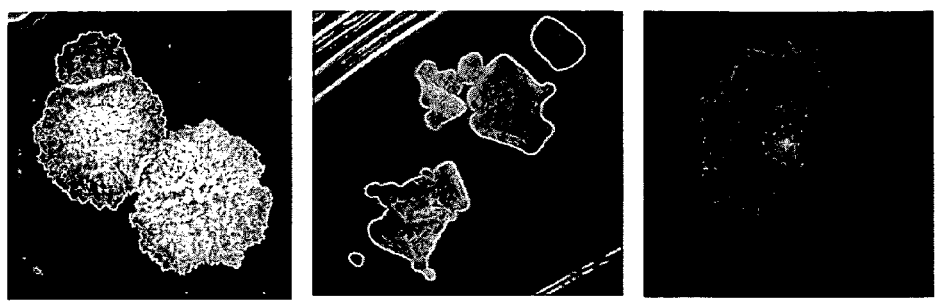
wild-type     Δ mmaA4     Δ mmaA4 complemented
B
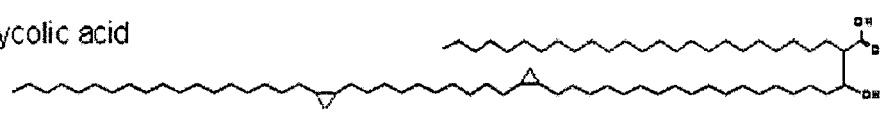
α-mycolic acid
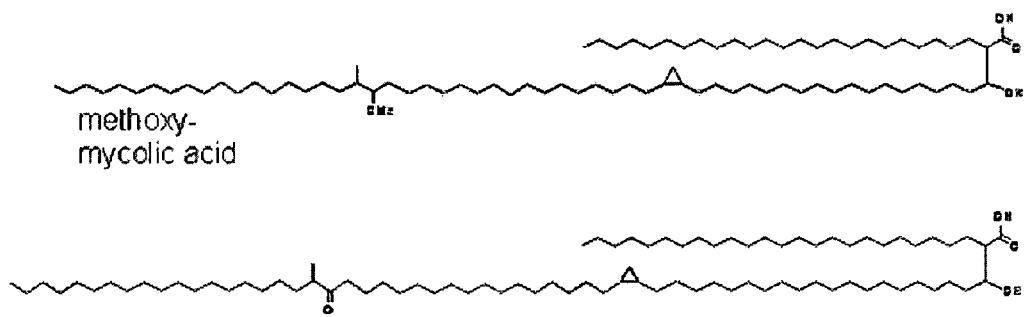
methoxy-mycolic acid
keto-mycolic acid FIG. 5
A
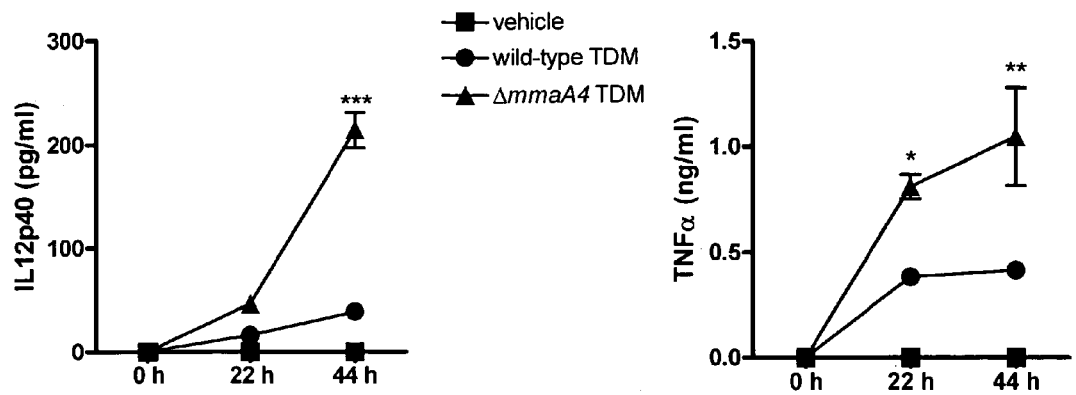
B
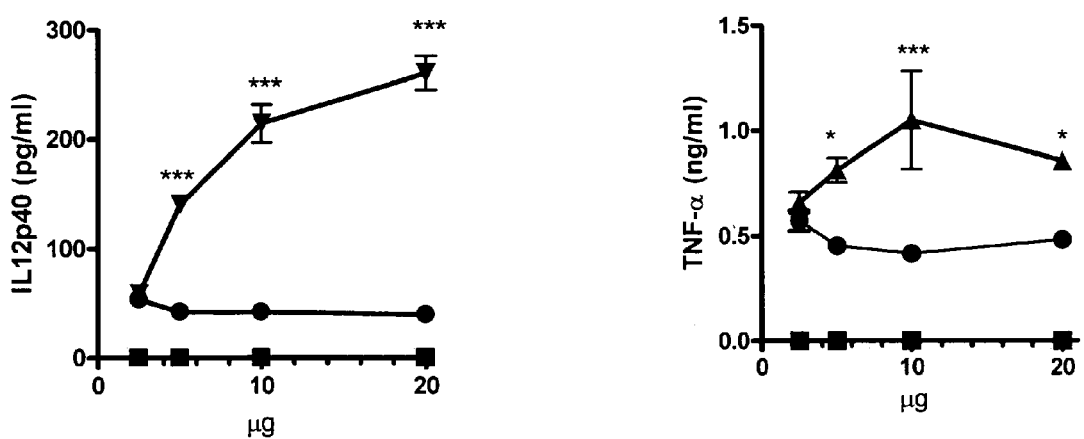

FIG. 8(A-B)
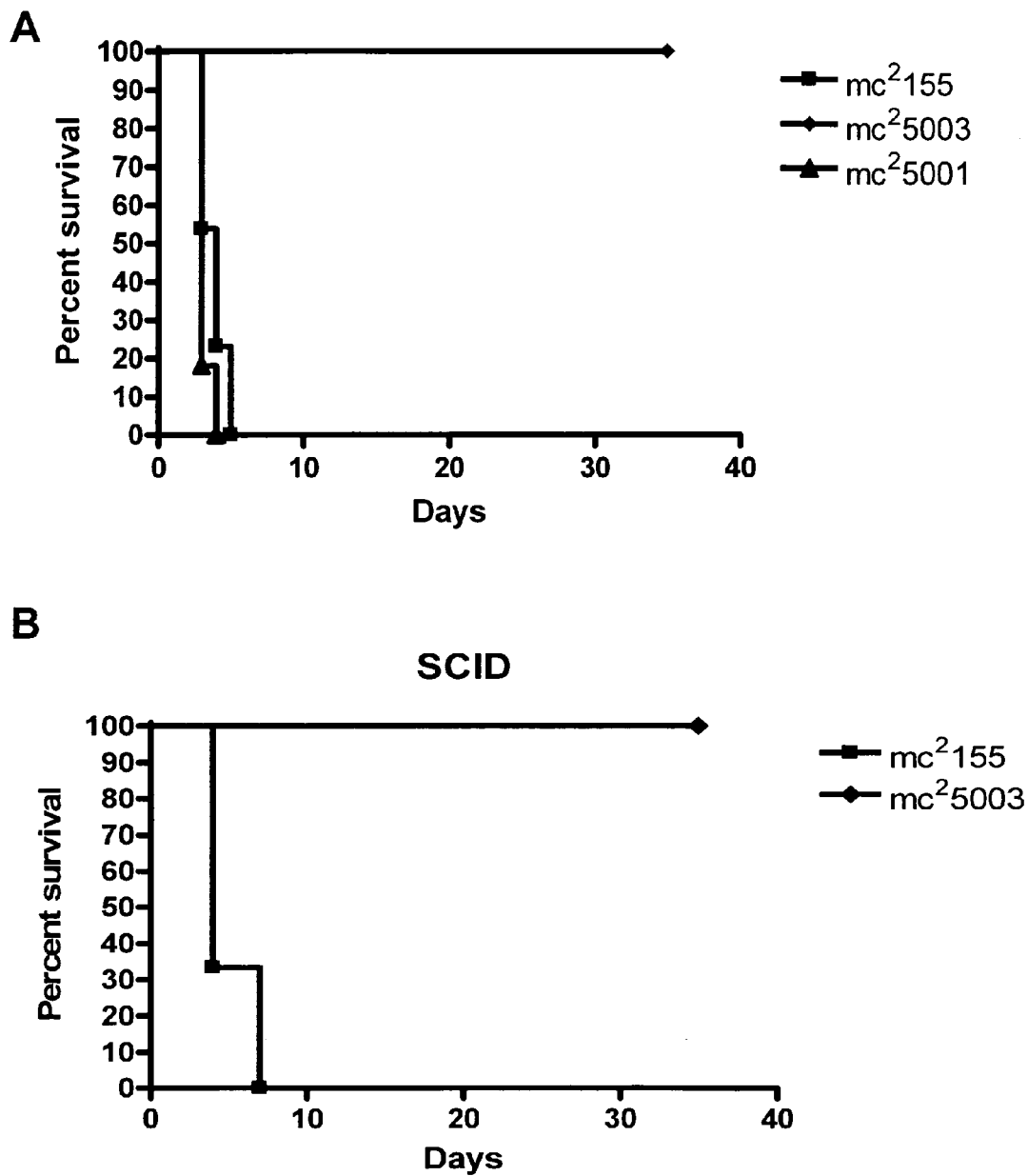

MYCOBACTERIAL MUTANTS INDUCING IL-12

CROSS-REFERENCE TO RELATED APPLICATIONS

This is a U.S. national phase of PCT Application No. PCT/US2008/003204, filed Mar. 10, 2008, which claims the benefit of U.S. Provisional Patent Application No. 60/918,997, filed on Mar. 19, 2007, and U.S. Provisional Patent Application No. 60/930,839, filed May 17, 2007, the contents of which are hereby incorporated by reference.

STATEMENT OF GOVERNMENT SUPPORT

This invention was made with government support under grant numbers AI52816, AI063537 and AI26170 awarded by the National Institutes of Health. The government has certain rights in the invention.

The ".txt" Sequence Listing filed by EFS, which is entitled 96700_1551.ST25, is 7 kilobytes in size and which was created on Dec. 13, 2011, is hereby incorporated by reference.

BACKGROUND OF THE INVENTION (1) Field of the Invention

The present invention generally relates to recombinant mycobacteria. More specifically, the invention is directed to mycobacteria that elicit IL-12 production in infected macrophages.

(2) Description of the Related Art

Tuberculosis (TB) is currently the second leading cause of death from a single infectious disease worldwide (Frieden et al., 2003; Onyebujoh and Rook, 2004). It is well established that *Mycobacterium tuberculosis* possesses a variety of mechanisms that promote enable evasion of innate immunity and permit latent infection in the presence of host adaptive immune responses (Flynn and Chan, 2003; Glickman and Jacobs, 2001; Flynn and Chan, 2001). This latent reservoir of *M. tuberculosis* can eventually develop into active disease when an individual's immune system is compromised due to aging, chemotherapy, or infection with HIV (Stead and Dutt, 1991; Kim et al., 2005; Ito et al., 2005; Campos et al., 2003). Currently, the attenuated *M. bovis* strain BCG is the only vaccine available for routine human immunization. It has had little if any impact on the increasing global prevalence of TB, in spite of having been administered to more than a billion people (Behr and Small, 1997). Thus, work on developing new and more immunogenic vaccine candidates is crucial and requires advances in our understanding of the host-pathogen interaction.

Cytokines play an important role in controlling intracellular infection, and the cytokine profile produced within the first days or weeks following infection can define the type of host immunity induced and, thereby, the outcome of the disease. A critical cytokine in the control of intracellular infections is interleukin-12 (IL-12), which is produced mainly by macrophages and dendritic cells (DCs) (Manetti et al., 1993; Trinchieri, 2003). IL-12 activates both early nonspecific innate immune resistance and subsequent antigen-specific adaptive immune responses. IL-12 is a growth factor for activated NK cells and induces them to produce IFNγ, a potent activator of macrophage bactericidal activity, while also inducing their cytotoxic activity. IL-12 also stimulates naïve T-cells, a component of adaptive immunity, to differentiate into IFN-γ producing T helper type 1 (Th1) cells.

IL-12p70, a dimer of IL-12p35 and IL-12p40, was originally thought to be the only bioactive form of IL-12 that activates both NK and T-cells to produce IFN-γ. It is now clear that other forms of IL-12 also have important immunoregulatory functions. Dimerization of IL-12p40 with the p19 subunit forms IL-23, which has IFN-γ inducing activity. The IL-12p40 subunit can also homodimerize, and recent studies indicate that the IL-12p40 homodimer is required for initiating adaptive immunity before IL-12p70 or IL-23 are produced (Khader et al., 2006). Thus, full activation of Th1 immunity is regulated by multiple cytokines containing the IL-12p40 subunit. The expression of the IL-12p40 subunit is regulated in infected myeloid cells, such as macrophages (Trinchieri, 2003), and it is known that mice and humans with mutations in the IL-12p40 gene or its cognate receptor are highly susceptible to mycobacterial infection (Altare et al., 2001; Altare et al., 1998; Jouanguy et al., 1999; de Jong et al., 1998; Cooper et al., 2002; Cooper et al., 1997; Cooper et al., 1995). However, other IL-12p40-related cytokines, such as IL-23 and their receptors, may be dispensable, since the survival rate of mice lacking these cytokines is comparable to that in wildtype mice following *M. tuberculosis* infection (Khader et al., 2005).

In the mouse model of infection, *M. tuberculosis* persists in macrophages even though induction of Th1 immunity is observed around 4 weeks post-infection (Flynn, 2004). Although bacterial growth slows and bacterial load eventually reaches a stable plateau as a result of adaptive immunity, the pathogen is not eliminated. Moreover, bacterial burden remains 2 to 3 orders of magnitude above that of attenuated strains of *M. tuberculosis*, such as H37Ra (Jung et al., 2002). Among other complications, the high bacterial burden and progressive chronic inflammation associated with it contribute to the death of the animal. While an effective Th1-mediated immune response generally develops following infection with intracellular pathogens such as *Salmonella* or *Toxoplasma gondii, M. tuberculosis* appears to evade eradication, in part by preventing the development of an effective Th1 response (Jung et al., 2002; Mastroeni, 2002; Gazzinelli et al., 1994). Studies of the mechanisms of immune evasion by *M. tuberculosis* have revealed that one of the strategies used by the tubercle *bacillus* is to repress macrophage production of IL-12p40 (Hickman et al., 2002; Nau et al., 2002). This parallels the paradigm proposed for *Leishmania* infection, in which repression of IL-12 production has been established as a key immune evasion strategy of the parasite (Reiner et al., 1994; McDowell and Sacks, 1999). Taken together, these findings suggest that during *M. tuberculosis* infection the host mounts a limited Th1 immune response that is insufficient to completely eliminate the tubercle bacterium, because specific determinants produced by *M. tuberculosis* modulate the host immune response.

ESAT-6 gene clusters. The primary attenuating mutation of bacillus Calmette-Guerin (BCG) was found to be a deletion (namely RD1), which was shown to encode two secreted proteins and their specific secretion system. These secreted proteins, ESAT-6 and Cfp-10, were first identified in culture filtrates of *M. tuberculosis* and shown to be immunodominant antigens. More recently, these proteins have been demonstrated to mediate necrosis of an infected cell which leads to egress of *M. tuberculosis* from the infected cells. Interestingly, ESAT-6 and Cfp-10 are part of a family of related homologues within *M. tuberculosis* and related orthologues in mycobacterial species (Gey van Pittius et al. 2001). Moreover, this family of proteins are found in all gram-positive organisms and deletion in *Staphylococcus* causes attenuation.

Based on the above, it would be useful to identify *mycobacterium* genes that affect host IL-12 production and to further characterize ESAT-6 and ESAT-6-like gene clusters, particularly with regard to virulence. The present invention addresses that need.

SUMMARY OF THE INVENTION

The inventors have identified two regions in *Mycobacterium* spp. that suppress IL-12 production in host macrophages.

The present invention is directed to mycobacteria deleted in at least a portion of a region 3 ESAT-6-like gene cluster (="R3"="ike"). With these mycobacteria, the deleted portion comprises at least genes analogous to ΔMs0615-0619 and ΔMs0622-0625 as identified in the GenBank *M. smegmatis* genome sequence nc_008596 Oct. 19, 2006 version.

The invention is also directed to recombinant mycobacteria comprising a mutation in a roc-1 gene. With these invention mycobacteria, the mutation increases the ability of the *mycobacterium* to induce IL-12 and/or TNF-α production in a mammalian macrophage infected by the *mycobacterium*. Here, the roc-1 gene without the mutation is at least 90% homologous to SEQ ID NO:1, and the *mycobacterium* is not a virulent *Mycobacterium tuberculosis*.

The invention is additionally directed to vaccines comprising any of the above-identified mycobacteria, with a vaccine adjuvant.

Also, the invention is directed to methods of making a recombinant *mycobacterium*. The methods comprise deleting at least a portion of a region 3 ESAT-6-like gene cluster, where the deleted portion comprises at least genes analogous to ΔMs0615-0619 and ΔMs0622-0625 as identified in the GenBank *M. smegmatis* genome sequence nc_008596 Oct. 19, 2006 version, wherein the *mycobacterium* is not an *M. tuberculosis*.

The invention is further directed to other methods of making a recombinant *mycobacterium*. The methods comprise genetically creating a mutation in a roc-1 gene, where the mutation increases the ability of the *mycobacterium* to induce IL-12 and/or TNF-α production in a mammalian macrophage infected by the *mycobacterium*, and where the roc-1 gene without the mutation is at least 90% homologous to SEQ ID NO:1, and wherein the *mycobacterium* is not a virulent *Mycobacterium tuberculosis*.

Also, the invention is directed to methods of inducing an immune response in a mammal. The methods comprise inoculating the mammal with any of the above-identified invention mycobacteria.

Additionally, the invention is directed to methods of inhibiting IL-12 production in a mammal. The methods comprise treating the mammal with purified mycolic acids from a virulent *Mycobacterium tuberculosis*.

The invention is also directed to other methods of inhibiting IL-12 production in a mammal. The methods comprise treating the mammal with a purified keto mycolic acid and/or methoxy mycolic acid.

The invention is additionally directed to methods of stimulating IL-12 production in a mammal. The methods comprise treating the mammal with purified mycolic acids from *Mycobacterium tuberculosis* Δroc-1.

Further, the invention is directed to other methods of stimulating IL-12 production in a mammal. The methods comprise treating the mammal with purified α-mycolic acid.

Additionally, the invention is directed to vaccine adjuvants comprising any of the above *mycobacterium*, purified mycolic acids from *Mycobacterium tuberculosis* Δroc-1, or purified α-mycolic acid.

The invention is further directed to vaccines comprising any of the above-described invention mycobacteria, purified mycolic acids from *Mycobacterium tuberculosis* Δroc-1, or purified α-mycolic acid.

Also, the invention is directed to vaccines to a target antigen. The vaccines comprise the target antigen and any of the above-described invention vaccine adjuvants.

The invention is further directed to methods of inducing immunity to a target antigen in a mammal. The methods comprise administering the above invention vaccine to the mammal.

BRIEF DESCRIPTION OF THE DRAWINGS

FIG. 3 is graphs showing increased induction of IL-12p40 (Panel A) and TNF-α (Panel B) by the ΔmmaA4 *M. tuberculosis* mutant in bone marrow-derived macrophages. Bone marrow-derived macrophages were infected at an MOI of 10 or left untreated (UT). The infecting bacteria were wildtype H37Rv, ΔmmaA4 mutant, or the complemented ΔmmaA4 strain. Conditioned media from macrophages was harvested at 24, 48, and 72 hr postinfection. IL-12p40 and TNF-α production were determined by ELISA. Values are statistically significant between wildtype and ΔmmaA4 mutant at 24, 48, and 72 hr ($p<0.001$ (***)); two-way ANOVA, Bonferroni post-tests. Values are the means±SD of samples and are representative of three separate experiments.

FIG. 5 is graphs of experimental results showing that purified TDM from the ΔmmaA4 mutant is sufficient to stimulate macrophages to produce IL-12p40. Panel A shows production of cytokines in bone marrow-derived macrophages over time; conditioned media was harvested at 22 and 44 hr post-TDM treatment. Vehicle treatment is the solvent in which the TDM was dissolved. Values are statistically significant between wildtype and the ΔmmaA4 mutant, as indicated by asterisks ($p<0.05$ (*), $p<0.01$ (), $p<0.001$ (*); two-way ANOVA, Bonferroni post-tests). Values are the means±SD of triplicate samples and are representative of three separate experiments performed on two independent batches of purified TDM from wildtype or mutant. Panel B shows a dose response to TDM purified from wildtype or ΔmmaA4 mutant. Bone marrow-derived macrophages were treated with varying doses of TDM purified from wildtype or ΔmmaA4 mutant. Conditioned media were assayed for cytokines at 44 hr. Values are statistically significant between wildtype and ΔmmaA4 mutant at the indicated dosages ($p<0.05$ (*), $p<0.001$ (**); two-way ANOVA, Bonferroni post-tests). Values are the means±SD of triplicate samples and are representative of two separate experiments performed on two independent batches of purified TDM.

DETAILED DESCRIPTION OF THE INVENTION

Figure 1A:
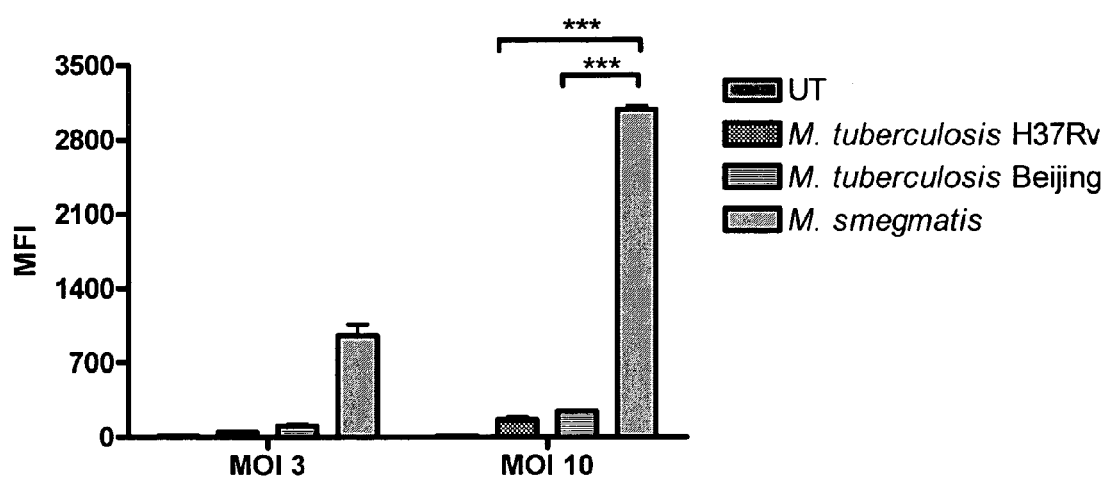
FIG. 1 is graphs and flow cytometry plots of the results of an evaluation of a stable IL-12p40 reporter macrophage cell line. Panel A shows the induction of IL-12p40 promoter activity in the macrophage reporter cell line in response to different mycobacterial strains. The Raw294::FLIL-12p40::GFP stable cell line was untreated (UT) or infected at an MOI of 3 or 10 with virulent *M. tuberculosis* Beijing/W (HN878) or H37Rv, or avirulent laboratory strain of *M. smegmatis* (mc$^2$155). GFP expression was measured by flow cytometry. Values are statistically significant between *M. smegmatis* and *M. tuberculosis* H37Rv ($p<0.001$) and similarly for *M. tuberculosis* Beijing ($p<0.001$); two-way ANOVA, Bonferroni post-tests. Values are the means±SD of triplicate samples and are representative of three separate experiments. For panel B, bone marrow-derived macrophages were infected at an MOI of 3 and an MOI of 10 with different strains of virulent *M. tuberculosis* (Beijing/W (HN878), H37Rv or with *M. smegmatis* (mc$^2$155). IL-12p40 from conditioned media was analyzed by ELISA. At an MOI of 10, *M. smegmatis* induced significantly more IL-12p40 than Beijing ($p<0.001$) and H37Rv ($p<0.001$); two-way ANOVA, Bonferroni post-tests. Values are the means±SD of samples and are representative of three separate experiments.

The inventors have identified two regions in *Mycobacterium* spp. that suppress IL-12 production in host macrophages. One region is the region 3 ESAT-6-like gene cluster (="R3"="ike") (Example 2). The other region is the roc-1 gene (=repressor of cytokine-1, also known as mmaA4, mma4, cmaA and hma) (Example 1). This discovery, and other discoveries related thereto, allows for the production of new mycobacteria that are useful in vaccines, as well as various methods of vaccine production and utilization, and treatment of diseases or conditions involving manipulation of IL-12 levels.

Thus, the present invention is directed to mycobacteria deleted in at least a portion of a region 3 ESAT-6-like gene cluster. With these mycobacteria, the deleted portion comprises at least genes analogous to ΔMs0615-0619 and ΔMs0622-0625 as identified in the GenBank *M. smegmatis* genome sequence nc_008596 Oct. 19, 2006 version, where the *mycobacterium* is not an *M. tuberculosis*. See Appendix 1 for a further identification of the *M. smegmatis* region 3 ESAT-6-like gene cluster. While the region 3 ESAT-6-like gene cluster comprises genes Ms0615-0625, a recombinant mutant described in Example 2 that was deleted in Ms0620-0621 did not have an effect on IL-12 production.

These invention mycobacteria can be of any *Mycobacterium* species now known or later discovered. Preferred mycobacteria are *M. smegmatis, M. bovis, M. avium, M. phlei, M. fortuitum, M. lufu, M. paratuberculosis, M. habana, M. scrofulacium, M. intracellulare,* or *M. kansasii*. Most preferably, the *mycobacterium* is an *M. smegmatis*.

As discussed in Example 2, when mycobacteria deleted in the region 3 ESAT-6-like gene cluster are further transfected with the *M. tuberculosis* region 3 ESAT-6-like gene cluster, production of IL-12 and other cytokines in infected macrophages is increased above the uncomplemented strain. Thus, preferably the invention *mycobacterium* deleted in at least a portion of a region 3 ESAT-6-like gene cluster is genetically complemented with at least genes analogous to ΔMs0615-0619 and ΔMs0622-0625 from an *M. tuberculosis*. More preferably, the *mycobacterium* is genetically complemented with at least genes analogous to ΔMs0615-0625 from *M. tuberculosis*, i.e., the entire region 3 ESAT-6-like gene cluster.

Most preferably, these invention mycobacteria induces higher expression of IL-12, TNF-α, or IFN-γ in a mammal when compared to the *mycobacterium* without the deletion. Where the *mycobacterium* is capable of causing disease, it is also preferred that the *mycobacterium* has attenuated virulence in a mammal when compared to the *mycobacterium* without the deletion.

These mycobacteria can also further comprise a recombinant gene operably linked to a promoter that directs expression of the gene when the *mycobacterium* infects a mammalian cell. Such mycobacteria are useful for, e.g., inducing immunity against the antigen. The recombinant gene can also encode an enzyme or other protein needed by a mammal that is to be inoculated with the *mycobacterium*. Preferably, the gene encodes an antigen, for example to a neoplasm, tumor or cancer, or to a human pathogen, to take advantage of the increased immunogenicity to the antigen as a result of the increased IL-12 production induced by the mutant. Examples of pathogens (e.g., human pathogens) where antigens useful in these mycobacteria include viruses (e.g., HIV, hepatitis C virus, herpes virus, influenza, smallpox, diphtheria, tetanus, measles, mumps, rabies, poliovirus, etc.), bacteria (e.g., pathogenic mycobacteria, *Salmonella* sp., etc.), and eukaryotic parasites (e.g., malaria, *Leishmania*, etc.).

The invention is also directed to recombinant mycobacteria comprising a mutation in a roc-1 gene. With these invention mycobacteria, the mutation increases the ability of the *mycobacterium* to induce IL-12 and/or TNF-α production in a mammalian macrophage infected by the *mycobacterium*. Here, the roc-1 gene without the mutation is at least 90% homologous to SEQ ID NO:1, and the *mycobacterium* is not a virulent *Mycobacterium tuberculosis*. Preferably, the mutation is a deletion. Most preferably, the deletion is a deletion of the entire roc-1 gene (Δroc-1).

These invention mycobacteria can be of any *Mycobacterium* species now known or later discovered, except for virulent *M. tuberculosis*. Preferred mycobacteria are *M. smegmatis, M. bovis, M. avium, M. phlei, M. fortuitum, M. lulu, M. paratuberculosis, M. habana, M. scrofulacium, M. intracellulare*, an attenuated or avirulent *M. tuberculosis*, or *M. kansasii*. More preferably, the *mycobacterium* is *M. bovis* BCG. Another particularly preferred *mycobacterium* is an *M. tuberculosis* H37ra.

A second gene can also be eliminated in these *mycobacterium*, wherein the *mycobacterium* exhibits attenuated virulence in a mammal when compared to the same *mycobacterium* expressing the second gene. A preferred second genes here is a portion of an RD1 region, or a gene controlling production of a vitamin or an amino acid. Other preferred second genes that can usefully be eliminated here are those where eliminating expression of the second gene increases the ability of the *mycobacterium* to induce apoptosis of a mammalian macrophage infected by the *mycobacterium*. Examples of such genes are nlaA genes, nuoG gene and a secA2 gene.

These mycobacteria can also further comprise a recombinant gene operably linked to a promoter that directs expression of the gene when the *mycobacterium* infects a mammalian cell. Such mycobacteria are useful for, e.g., inducing immunity against the antigen. The recombinant gene can also encode an enzyme or other protein needed by a mammal that is to be inoculated with the *mycobacterium*. Preferably, the gene encodes an antigen, for example to a neoplasm, tumor or cancer, or to a human pathogen, to take advantage of the increased immunogenicity to the antigen as a result of the increased IL-12 production induced by the mutant. Examples of pathogens (e.g., human pathogens) where antigens useful in these mycobacteria include viruses (e.g., HIV, hepatitis C virus, herpes virus, influenza, smallpox, diphtheria, tetanus, measles, mumps, rabies, poliovirus etc), bacteria (e.g., pathogenic mycobacteria, *Salmonella* sp., etc.), and eukaryotic parasites (e.g., malaria, *Leishmania*, etc.).

The present invention is also directed to vaccines comprising any of the above invention mycobacteria, with a vaccine adjuvant. The skilled artisan could select a suitable adjuvant for these vaccines without undue experimentation. Preferred vaccine adjuvant is purified mycolic acids from *Mycobacterium tuberculosis* Δroc-1 or purified α-mycolic acid (see below and Example 1).

Also, the invention is directed to methods of making a recombinant *mycobacterium*. The methods comprise deleting at least a portion of a region 3 ESAT-6-like gene cluster, where the deleted portion comprises at least genes analogous to ΔMs0615-0619 and ΔMs0622-0625 as identified in the GenBank *M. smegmatis* genome sequence nc_008596 Oct. 19, 2006 version, wherein the *mycobacterium* is not an *M. tuberculosis*. The deletion is preferably made by recombinant methods allowing for insertion of a vector into the region 3 by homologous recombination, for example as described in the examples. Most preferably, the entire region 3 ESAT-6-like gene cluster, i.e., ΔMs0615-0625, is deleted. See Example 2 for non-limiting examples of these invention mycobacteria. These methods can be utilized with any mycobacteria, either wild-type or recombinant, e.g., with other attenuating mutations and/or foreign antigens. Preferably, the *mycobacterium* is an *M. smegmatis*.

The invention is further directed to other methods of making a recombinant *mycobacterium*. The methods comprise genetically creating a mutation in a roc-1 gene, where the mutation increases the ability of the *mycobacterium* to induce IL-12 and/or TNF-α production in a mammalian macrophage infected by the *mycobacterium*, and where the roc-1 gene without the mutation is at least 90% homologous to SEQ ID NO:1, and wherein the *mycobacterium* is not a virulent *Mycobacterium tuberculosis*. Example 1 provides exemplary methods for making these recombinant mycobacteria. These methods can be utilized with any mycobacteria, either wild-type or recombinant, e.g., with other attenuating mutations and/or foreign antigens. Preferably, the *mycobacterium* is an *M. tuberculosis*.

Since the invention mycobacteria described above generally induce IL-12 production, they are useful for inducing an immune response in a mammal, for example to the *mycobacterium* itself, e.g., as a tuberculosis vaccine, or to a recombinant antigen expressed by the *mycobacterium* or present with the *mycobacterium*. Thus, the present invention is also directed to methods of inducing an immune response in a mammal. The methods comprise inoculating the mammal with any of the above-identified invention mycobacteria.

As discussed in Example 1, purified trehalose 6'-6' dimycolates from a virulent *Mycobacterium tuberculosis* inhibit IL-12 production. Administration of these trehalose 6'-6' dimycolates are therefore useful where IL-12 production is excessive or otherwise unwanted. Therefore, the invention is additionally directed to methods of inhibiting IL-12 production in a mammal. The methods comprise treating the mammal with purified trehalose 6'-6' dimycolates from a virulent *Mycobacterium tuberculosis*.

As used herein, "purified" means present in a greater concentration than would be found in nature, e.g., in an *M. tuberculosis*. Preferably, an isolated and purified mycolic acid is at least about 10% of the solute, non-salt component of the trehalose 6'-6' dimycolates preparation; more preferably at least about 25%; even more preferably at least about 50%; still more preferably at least about 75%; and most preferably at least about 90% of the solute, non-salt component of the preparation.

Preferably, the trehalose 6'-6' dimycolate preparation here is in a pharmaceutically acceptable preparation. By "pharmaceutically acceptable" it is meant a preparation that (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, water, emulsions such as oil/water emulsions, microemulsions, and the like.

The above-described compounds can be formulated without undue experimentation for administration to a mammal, including humans, as appropriate for the particular application. Additionally, proper dosages of the compositions can be determined without undue experimentation using standard dose-response protocols.

Accordingly, the preparations designed for oral, lingual, sublingual, buccal and intrabuccal administration can be made without undue experimentation by means well known in the art, for example with an inert diluent or with an edible carrier. The preparations may be enclosed in gelatin capsules or compressed into tablets. For the purpose of oral therapeutic administration, the pharmaceutical preparations of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The preparations can easily be administered parenterally such as for example, by intravenous, intramuscular, intrathecal or subcutaneous injection. Parenteral administration can be accomplished by incorporating the trehalose 6'-6' dimycolates into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the trehalose 6'-6' dimycolates, in a pharmaceutical composition, into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the trehalose 6'-6' dimycolates through the skin. Transdermal formulations include patches (such as the well-known nicotine patch), ointments, creams, gels, salves and the like.

The present invention includes nasally administering to the mammal a therapeutically effective amount of the trehalose 6'-6' dimycolates. As used herein, nasally administering or nasal administration includes administering the compound to the mucous membranes of the nasal passage or nasal cavity of the patient. As used herein, pharmaceutical compositions for nasal administration of the compound include therapeutically effective amounts of the compound prepared by well-known methods to be administered, for example, as a nasal spray, nasal drop, suspension, gel, ointment, cream or powder. Administration of the compound may also take place using a nasal tampon or nasal sponge.

The invention is also directed to other methods of inhibiting IL-12 production in a mammal. The methods comprise treating the mammal with a purified keto and/or methoxy mycolate esterified to trehalose. As indicated in Example 1, keto and/or methoxy mycolate esterified to trehalose are the primary components of trehalose 6'-6' dimycolates from a virulent *Mycobacterium tuberculosis*, which inhibit host IL-12 production. Preferably, the mammal is a human.

In some aspects of these methods, the mammal has an autoimmune disease. Autoimmune diseases are known to be exacerbated by IL-12. Thus, a treatment that inhibits IL-12 production is useful for administering to a patient with an autoimmune disease. Non-limiting examples of autoimmune diseases here is multiple sclerosis, systemic lupus erythematosus, rheumatoid arthritis, autoimmune pulmonary inflammation, Guillain-Barre syndrome, autoimmune thyroiditis, insulin dependent diabetes mellitus and autoimmune inflammatory eye disease.

As discussed in Example 2, besides IL-12, *M. tuberculosis* also inhibits host production of the proinflammatory cytokines TNF-$\alpha$ and IFN-$\gamma$. Thus, administration of purified mycolic acids from *M. tuberculosis* or keto and/or methoxy mycolate esterified to trehalose is useful for administration to a mammal at risk for or having a condition mediated by a proinflammatory cytokine. Examples of such conditions include appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis, hepatitis, Crohn's disease, ileus, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillain-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, Retier's syndrome, or Hodgkins disease.

The inventors have also discovered that administration of purified trehalose 6'-6' dimycolates from *Mycobacterium tuberculosis* Δroc-1 stimulates IL-12 production by the host. Thus, the invention is additionally directed to methods of stimulating IL-12 production in a mammal. The methods comprise treating the mammal with purified trehalose 6'-6' dimycolates from *Mycobacterium tuberculosis* Δroc-1.

Since α- or epoxy mycolates esterified to trehalose is the primary mycolic acid in *Mycobacterium tuberculosis* Δroc-1, treating a mammal with purified α- or epoxy mycolates esterified to trehalose is also useful for stimulating IL-12 production. Thus, the invention is further directed to methods of stimulating IL-12 production in a mammal. The methods comprise treating the mammal with purified α- or epoxy mycolate esterified to trehalose.

Stimulation of IL-12 production is useful for inducing immunity. Therefore, purified trehalose 6'-6' dimycolates from *Mycobacterium tuberculosis* Δroc-1 or purified α- or epoxy mycolates esterified to trehalose are useful as a vaccine adjuvant. Thus, the purified trehalose 6'-6' dimycolates from *Mycobacterium tuberculosis* Δroc-1 or purified α- or epoxy mycolates esterified to trehalose for these methods is preferably in a vaccine adjuvant.

Stimulation of IL-12 production is known to be useful for treating infections or cancer. These methods can therefore be used where the mammal has an infection. They can also be used where the mammal has cancer.

The invention is also directed to a vaccine adjuvant comprising any of the above-described invention mycobacteria. Additionally, the invention is directed to a vaccine adjuvant comprising purified trehalose 6'-6' dimycolates from *Mycobacterium tuberculosis* Δroc-1. Further, the invention is directed to a vaccine adjuvant comprising purified α- or epoxy mycolate esterified to trehalose.

The invention is further directed to vaccines comprising any of the above-described invention mycobacteria, purified trehalose 6'-6' dimycolates from *Mycobacterium tuberculosis* Δroc-1, or purified α- or epoxy mycolate esterified to trehalose.

Also, the invention is directed to vaccines to a target antigen. The vaccines comprise the target antigen and any of the above-described invention vaccine adjuvants.

The invention is further directed to methods of inducing immunity to a target antigen in a mammal. The methods comprise administering the above invention vaccine to the mammal.

The region 3 ESAT-6-like gene cluster or the roc-1 gene can also be targets for drug development. In these aspects of the invention, an anti-mycobacterial drug could be identified by screening compounds (including small organic molecules or macromolecules like antibodies or aptamers) for the ability to eliminate expression of the roc-1 gene or relevant genes in the region 3 ESAT-6-like gene cluster.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1

Mycolic Acids of Trehalose Dimycolate Modified by mmaA4 Repress IL-12p40 Production Example Summary

*Mycobacterium tuberculosis* has evolved many strategies to evade elimination by the host immune system and establish a chronic infection. One method of immune evasion is to repress IL-12p40 production by macrophages. To identify the factors responsible for repression of macrophage IL-12p40 production by *M. tuberculosis*, we screened a transposon library of *M. tuberculosis* for mutants that lacked this function using a macrophage cell line expressing a reporter for IL-12p40 transcription. This approach led to the identification of the *M. tuberculosis* mmaA4 gene as a key locus involved in the repression of IL-12p40. Mutants in which the mmaA4 gene was inactivated produce significantly more IL-12p40 and TNF-α as compared to wildtype *M. tuberculosis*. The mmaA4 gene encodes an S-adenosylmethionine dependant methyl transferase required for the synthesis of methoxy and keto mycolic acids, which are abundant lipids among which some are secreted as a component of the glycolipid trehalose 6,6'-dimycolate (TDM). The ΔmmaA4 mutant is defective in synthesis of oxygenated mycolates. Studies using TDM purified from the ΔmmaA4 mutant showed increased IL-12p40 secretion from treated macrophages, similar to the increase observed from ΔmmaA4 mutant infected macrophages. In contrast, purified TDM isolated from wildtype *M. tuberculosis* represses IL-12p40 secretion from treated macrophages. These results indicate that the oxygen-containing substitutions on mycolic acids negatively regulate IL-12p40 production, and identified a new immunoregulatory role for TDM as a repressor of macrophage IL-12p40 production. The identification of this function for the mmaA4 gene provides a genetic basis for an important aspect of immune evasion by *M. tuberculosis*, and may have significant implications for approaches to engineering more immunogenic attenuated vaccine strains of this organism.

ABBREVIATIONS

TDM, trehalose dimycolate; mmaA4, methyl transferase 4; hma, hydroxymycolic acid; LPS, lipopolysaccharide; TLR, Toll-like receptor.

Introduction

Based on the evidence that the amount of IL-12 produced is a good correlate of protective immunity (Manca et al., 1999), that IL-12 therapy decreases bacterial burden and extends survival in patients or mice infected with TB (Greinert et al., 2001; Flynn et al., 1995; Holscher et al., 2001), and that M. tuberculosis represses IL-12p40 production (Hickman et al., 2002; Nau et al., 2002), it was hypothesized that M. tuberculosis actively modulates the production of this cytokine in infected macrophages. To identify genes responsible for this, a transposon library of M. tuberculosis mutants was screened using a macrophage cell line expressing a reporter gene for monitoring IL-12p40 expression. The mmaA4 gene is identified here as a locus in M. tuberculosis involved in the repression of IL-12 production in infected macrophages. Additionally, it is shown that inactivation of the mmaA4 gene by targeted deletion caused production of mycolic acids that lacked methoxy and keto functional groups. The mycobacterial component eliciting this increase in cytokine production from the infecting ΔmmaA4 mutant was identified as trehalose 6,6'-dimycolate (TDM), which is devoid of keto- and methoxy-mycolic acids. In contrast to TDM from wildtype M. tuberculosis, which repressed IL-12p40 production by macrophages, purified TDM from the ΔmmaA4 mutant stimulated macrophage IL-12p40 production. Our data establish the role of the MmaA4-derived oxygenated mycolic acids of TDM in the repression of IL-12p40 production, thus establishing part of the genetic and mechanistic basis for an important aspect of the immune evasion strategy of M. tuberculosis.

Results

Isolation of a Mutant Defective in Repression of IL-12p40 Production by Infected Macrophages.

To isolate mutants that are defective in IL-12p40 suppression, a macrophage reporter cell line was generated to monitor IL-12p40 expression. Previously, a macrophage reporter cell line was described containing a minimal IL-12p40 promoter fused to GFP that was stably integrated into the genome (Dao et al., 2004). Since the regulation of the IL-12p40 promoter in response to M. tuberculosis infection is not known, for this screen another macrophage cell line was engineered containing a stable integration of the full-length IL-12p40 promoter fused to GFP. Detailed analysis by flow cytometry of this reporter cell showed that GFP levels accurately reflected IL-12p40 production from the endogenous locus. GFP was not transcribed in uninfected macrophages until treated with lipopolysaccharide (LPS) or infected with E. coli (data not shown). A flow cytometric assay of GFP expression after infection with mycobacterial strains that varied in their virulence showed that induction of GFP followed a similar pattern to what was observed using a capture ELISA to quantitate IL-12 p40 levels in supernatants of infected bone marrow-derived macrophages (FIGS. 1A and 1B). The levels of IL-12p40 that was found in M. tuberculosis H37Rv and Beijing strains replicated the results of other groups (Chacon-Salinas et al., 2005; Manca et al., 1999).

Figure 2:
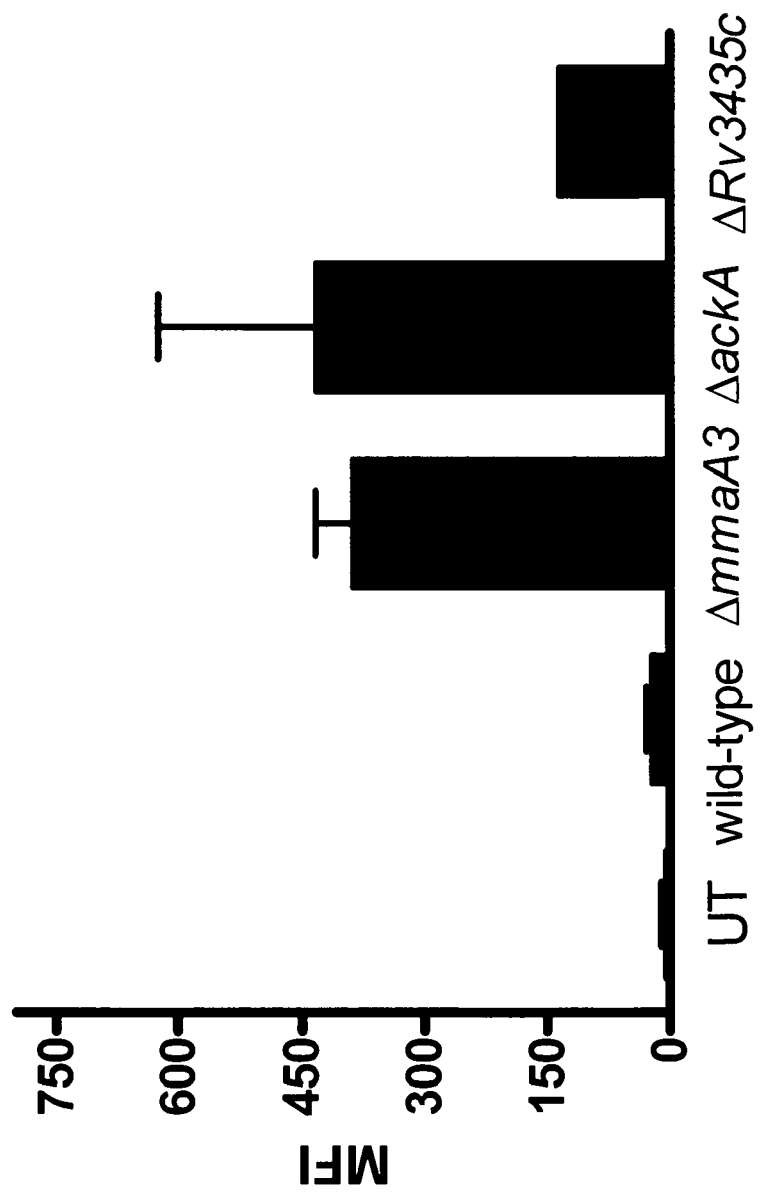
FIG. 2 is a graph of flow cytometry results of *M. tuberculosis* H37Rv mutants that induced increased levels of IL-12p40. A secondary screen on the candidates was performed by flow cytometry. Expanded cultures were used to infect the Raw294::FL.IL-12p40::GFP macrophage reporter cell line at an MOI of 10. Values are the means±SD of duplicate samples and are representative of two separate experiments.

It was reasoned that the loss of determinants that repress IL-12p40 would cause the mutant to induce elevated levels of IL-12p40. To isolate mutants that induce IL-12p40, a Himar-1 transposon library of the sequenced M. tuberculosis H37Rv strain was created and arrayed in 96-well plates. This transposon was used to generate M. tuberculosis mutants because it inserts randomly into frequently-occurring TA dinucleotides (Rubin et al., 1999). Approximately 2880 transposon mutants were screened by fluorimetric assay of macrophages expressing the IL-12 p40-GFP reporter to identify wells in which GFP expression was greater than a baseline established by wildtype H37Rv infection. From this primary screen three mutants were identified that gave enhanced GFP signals. These were found by sequencing to have transpositions in the mmaA3, ackA, and Rv3435c genes. The insertional mutant of mmaA3, which encodes an S-adenosylmethionine-dependent methyl transferase known to be involved in the modification of M. tuberculosis mycolic acids (Takayama et al., 2005), gave the highest GFP expression with our secondary screen, as compared to wildtype (FIG. 2B), as determined by FACS analysis. The ΔackA and ΔRv3435c mutants did not induce consistent IL-12p40 production in bone marrow-derived macrophages after tertiary screen by ELISA, and these mutants were not analyzed further.

Focusing on the mutant with an insertion in the mmaA3 gene, specialized transduction (Bardarov et al., 1997; Bardarov et al., 2002) was used to generate an independent deletion mutant of this gene. Since the mmaA3 gene is upstream of the mmaA4 gene that is also known to encode a methyl transferase that acts on mycolic acids, and the transcriptional regulation of this locus could have been compromised by the transposon insertion, a strain with deletion of the mmaA4 gene was also generated. Findings for the ΔmmaA3 and the ΔmmaA4 mutants are described here.

Increased Induction of IL-12p40 by Macrophages Infected with the ΔmmaA4 Mutant.

To confirm the findings from the IL-12p40 macrophage reporter assays, the cytokines produced in conditioned media of bone marrow-derived macrophages infected with either the ΔmmaA3 or ΔmmaA4 mutants were examined. Macrophages infected with the ΔmmaA3 mutant showed variable increases in IL-12p40 production, as compared to those observed for the ΔmmaA4 mutant (data not shown). Moreover, the ΔmmaA3 mutant, when grown on agar plates, showed both rough and smooth colonial morphology (data not shown). This phenotypic switching was found to be reversible upon subsequent sub-cloning. Because the switching between the two morphologies was a potential confounding variable that could affect IL-12p40 induction, no additional studies were pursued with the ΔmmaA3 mutant. On the other hand, the ΔmmaA4 mutant maintained a stable smooth colony morphology with routine passage (FIG. 4A). The growth rate of the ΔmmaA4 mutant in liquid culture was also found to be equivalent to wild type (data not shown).

Macrophages infected with the ΔmmaA4 mutant showed a reproducible increase in both IL-12p40 and TNF-α production (FIG. 3). To prove that the increased cytokine production was due to the loss of the mmaA4 gene, we tested the complemented mutant. As seen in FIG. 3, when a copy of the mmaA4 gene was restored in the ΔmmaA4 mutant, IL-12p40 and TNF-α production were reduced to levels comparable to that of the parental M. tuberculosis strain H37Rv. IL-12p40 production in macrophages infected with the ΔmmaA4 mutant increased over time. Initially at 24 hr there was a 2-fold increase over wildtype, but by 72 hr this increase had grown to 4-fold. Induction of TNF-α maintained the 2-fold increase throughout the interval tested.

The mmaA4 Gene Encodes an Enzyme Involved in Modification of Methoxy- and Keto-Mycolic Acids.

When the ΔmmaA4 mutant was plated on media containing the detergent Tween-80, a smooth colony morphology with ruffled edges was observed. This was distinctly different from the rough morphology observed with wildtype *M. tuberculosis* after 1 month of growth on plates. This difference in colony morphology was reversed by complementation of the ΔmmaA4 mutant (FIG. 4A). However, in the absence of Tween-80, there was no difference in morphology between the wildtype and the mutant (data not shown). Since Tween-80 most likely exerts its effects on colony morphology by interacting with the lipids on the cell wall to alter surface tension with the media surface (Van Boxtel et al., 1990), these findings suggest that inactivation of the mmaA4 gene led to alterations in the lipid composition of the bacterial cell wall. Given that mmaA4 (also known as hma) has previously been implicated in the synthesis and modification of mycolic acids, we then carefully examined the features of this major class of lipids in the ΔmmaA4 mutant.

Figure 4C:
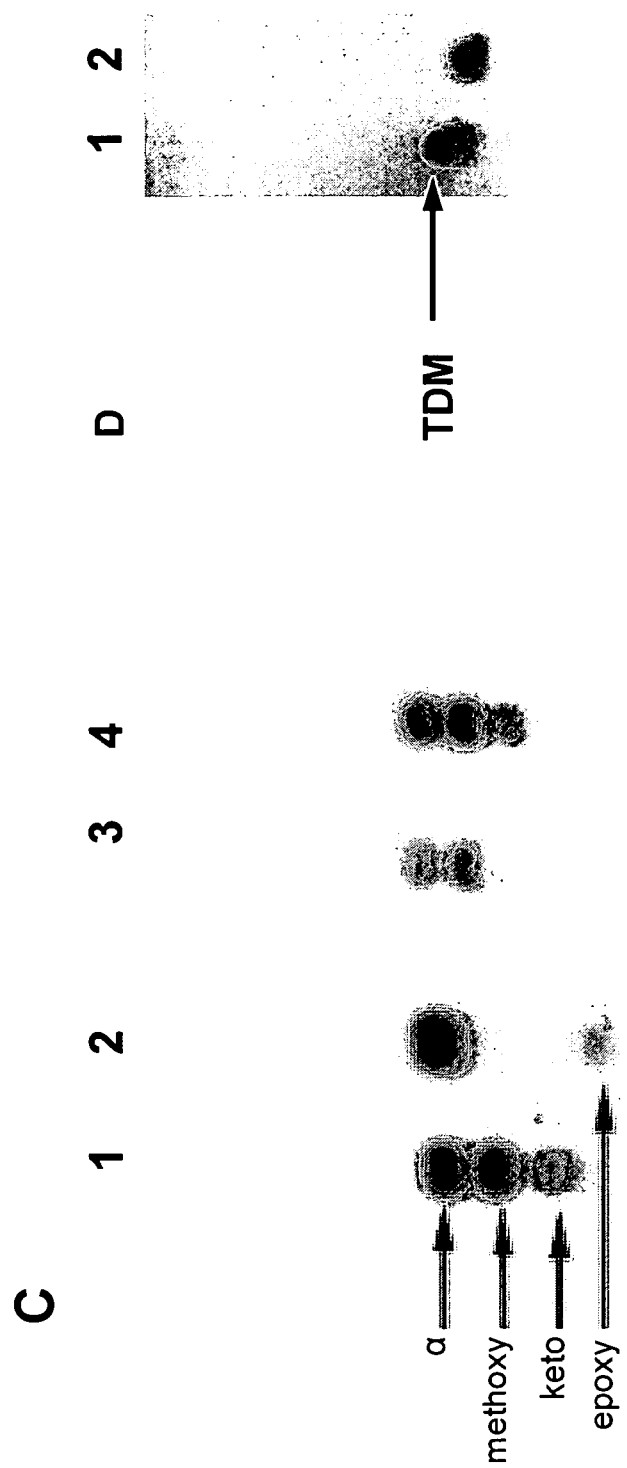
FIG. 4 is photographs of mycobacterial colonies, chemical structures of mycolic acids, and photographs of a thin-layer chromatographic analysis showing changes in colonial morphology and loss of methoxy- and keto-oxygenated mycolic acids following deletion of mmaA4 gene. Panel A shows wildtype *M. tuberculosis* H37Rv, the ΔmmaA4 *M. tuberculosis* mutant, and the complemented ΔmmaA4 *M. tuberculosis* strain were all grown on 7H10 plates containing 0.5% Tween 80. Pictures of the colonies were taken after 1 month of growth. Panel B shows a schematic representation of alpha-, methoxy-, and keto-mycolic acids derived from the wildtype *M. tuberculosis* H37Rv strain. Panel C shows the results of a thin-layer chromatographic analysis of lipids extracted from [$^{14}$C] acetate labeled cultures of wildtype H37Rv, the ΔmmaA4 *M. tuberculosis* mutant, and the complemented ΔmmaA4 *M. tuberculosis*. The cultures were grown to mid-exponential phase in 7H9 containing Tween 80 media, at which time [$^{14}$C] acetate was added, and were incubated for an additional 12 hr. Lipids were then extracted from cultures for analysis. MAMEs were analyzed by 1D-High Performance Thin-Layer Chromatography (1D-HPTLC), using two developments of hexane/ethyl acetate [95:5]) and visualized by autoradiography. Lane 1, wildtype H37Rv; lane 2, ΔmmaA4 mutant; Lane 3, wildtype H37Rv; lane 4, ΔmmaA4 mutant complemented. Panel D shows the results of a thin-layer chromatographic analysis of purified TDM from wild-type and ΔmmaA4 mutant *M. tuberculosis* developed with chloroform/methanol/water (90:10:1, vol/vol/vol). Lane 1, wildtype H37Rv; lane 2, ΔmmaA4 mutant.

Mycolic acids are long-chain α-alky β-hydroxy fatty acids unique to mycobacteria. Three distinct structural classes of mycolic acids (alpha-, methoxy-, and keto-mycolic acids) are an integral part of the *M. tuberculosis* outer cell envelope (FIG. 4B) (Takayama et al., 2005). The meromycolate chains of alpha-mycolic acids are modified with cyclopropane groups, whereas the methoxy- or keto-mycolic acids are modified with methoxy or carbonyl groups, respectively. We ascertained the mycolic acid profiles of wildtype H37Rv, the ΔmmaA4 mutant, and the complemented ΔmmaA4 mutant strain (FIG. 4C). Thin-layer chromatographic analysis of lipids extracted by organic solvents from the wild type and the ΔmmaA4 mutant confirmed that wildtype H37Rv synthesized all three types of mycolic acids. Unlike wildtype, the ΔmmaA4 mutant synthesized alpha-mycolic acids but failed to produce mycolic acids containing methoxy and keto functional groups. In addition, the ΔmmaA4 mutant acquired a new class of mycolic acids, epoxy-mycolates, although they represented only a minor fraction of the total mycolic acid composition. Complementation of the ΔmmaA4 mutant restored the mycolic acid profile to that of the wild type (FIG. 5C).

Trehalose 6,6'-Dimycolate (TDM) Purified from the mmaA4 Mutant is Sufficient to Elicit the Increase in IL-12p40 and TNF-α Production.

Mycolic acids can be esterified at the 6 and 6' carbon positions of the disaccharide trehalose to form trehalose 6,6'-dimycolate (TDM), which is an abundant mycobacterial glycolipid that is secreted into the cytoplasm of infected macrophages (Takayama et al., 2005: Geisel et al., 2005). Since TDM is known to have direct effects on macrophages (Rao et al., 2005; Tao et al., 2006; Rhoades et al., 2003), it was hypothesized that TDM from the ΔmmaA4 mutant could be considered a good candidate for regulation of IL-12p40. TDM was purified to homogeneity by thin-layer chromatography from wild type and ΔmmaA4 mutant bacteria (FIG. 4D), and was shown to be endotoxin-free using the limulus assay. We tested purified TDM from both the mutant (ΔmmaA4TDM) and wildtype H37Rv (wtTDM) for its ability to induce IL-12p40 and TNF-α. IL-12p40 production was detected at 22 hr in conditioned media from macrophages that were treated with ΔmmaA4TDM, and further increased 4-fold by 44 hr (FIG. 5A). TNF-α was detected at 22 hr, with no further increase thereafter (FIG. 5B). In contrast, a statistically insignificant change in IL-12p40 production was observed for wtTDM after 22-44 hr of incubation (FIG. 5A). IL-12p40 and TNF-α production by macrophages treated with ΔmmaA4TDM was dose-dependent, whereas wtTDM did not show a dose dependency over the range of TDM concentration tested (FIG. 5B). These findings suggested that the increased macrophage cytokine production seen with ΔmmaA4 mutant infection was mediated by the ΔmmaA4TDM glycolipid.

TDM from Wild Type *M. tuberculosis* is a Negative Regulator of IL-12p40 Production in Macrophages.

The finding that wtTDM induced only baseline levels of IL-12p40 over the wide range tested, while ΔmmaA4TDM strongly induced IL-12p40 production, led to the hypothesis that the wtTDM having oxygen-containing methoxy and keto groups was negative regulator of IL-12p40 production. To test this idea, a lipid competition assay between wtTDM and ΔmmaA4TDM was performed, in which macrophages were treated with a mixture of both glycolipids. Reduction of IL-12p40 was observed in macrophages treated with the glycolipid mixture (FIG. 5A). This suppression was specific for IL-12p40, as TNF-α production by these treated macrophages was not affected (FIG. 5A).

Figure 6:
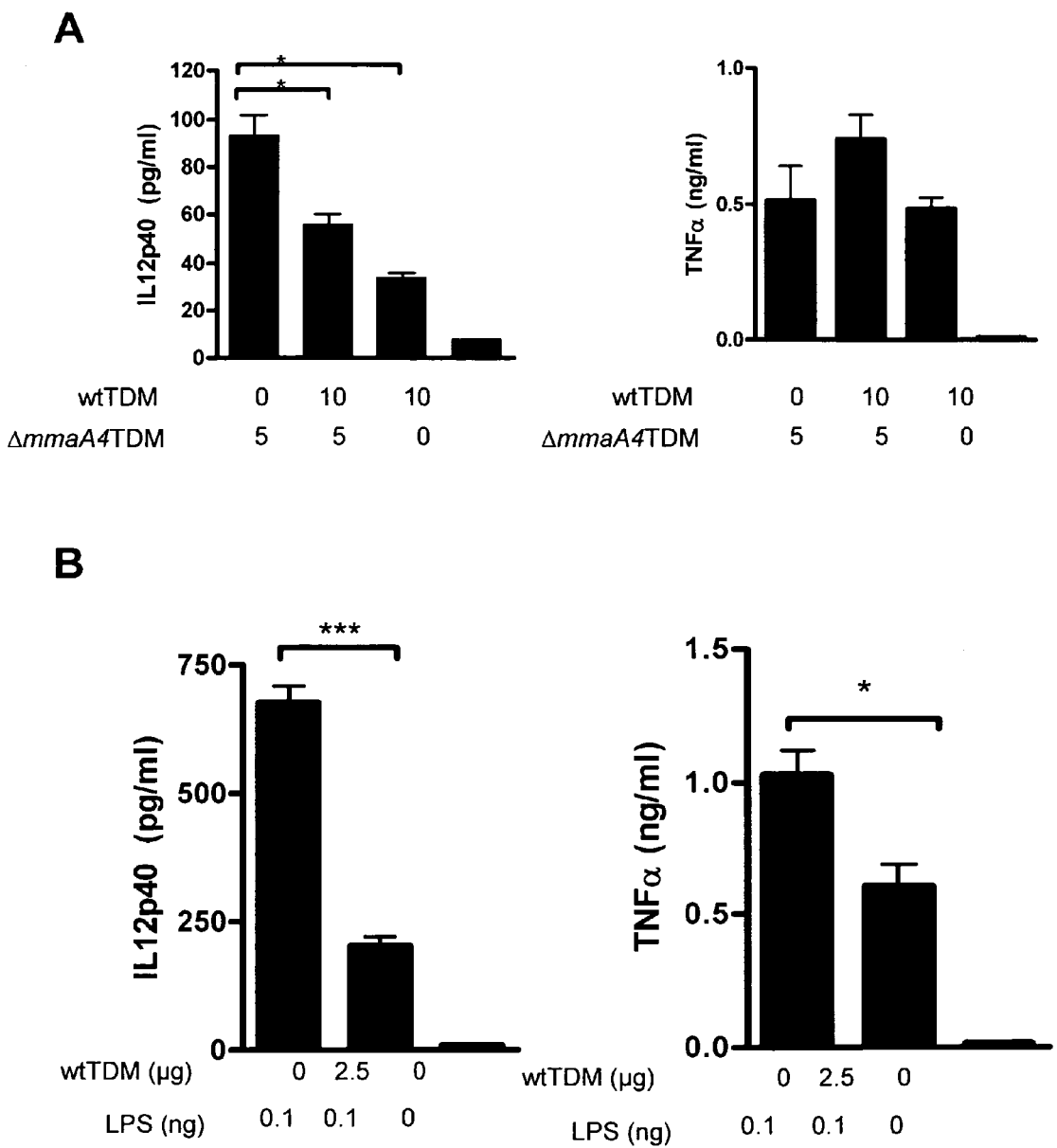
FIG. 6 is graphs of experimental results showing that purified wildtype *M. tuberculosis* trehalose 6,6'-dimycolate (TDM) suppresses macrophage IL-12p40 induction. Cytokines were analyzed by ELISA from conditioned media harvested at 24 hr. Values are the means±SD of triplicate samples and are representative of two separate experiments. In panel A, bone marrow-derived macrophages were incubated with ΔmmaA4TDM alone or in the presence of purified wildtype (wt) TDM in conjunction with ΔmmaA4TDM. Asterisk indicates values are statistically significant ($p<0.05$ (*); one-way ANOVA, Bonferroni post-tests). In panel B, bone-marrow derived macrophages were treated with lipopolysaccharide (LPS) alone or a mixture of TDM purified from wildtype *M. tuberculosis* and LPS. Asterisk indicates values are statistically significant ($p<0.05$ (*), $p<0.001$ (***); one-way ANOVA, Bonferroni post-tests).

We reasoned that if TDM actively represses IL-12p40 production, this repression should be observed in the presence of other agonists of IL-12p40 production. Lipopolysaccharide (LPS) is a bacterial pathogen-associated molecular pattern (PAMP) that induces a potent IL-12p40 response when added to macrophages. wtTDM inhibited LPS induction of IL-12p40 3-4-fold (FIG. 6B). A minor but statistically significant suppression of TNF-α production was also observed (FIG. 6B). Taken together, these data suggest that the keto and methoxy groups on the TDM are negative regulators of IL-12p40 production.

Discussion

This work was designed to investigate the components of *Mycobacterium tuberculosis* that modulate the host immune response. To this end, a screen for mutants was developed that interfered with the production of macrophage IL-12p40, a cytokine important for activating innate and adaptive immunity against intracellular pathogens. This approach led to the discovery of the *M. tuberculosis* mmaA4 gene as a key locus involved in modulation of IL-12p40. Loss of the mmaA4 gene in *M. tuberculosis* H37Rv induced infected macrophages to produce more IL-12p40, and that this inducing activity was linked to its TDM. In contrast, TDM from wildtype *M. tuberculosis* represses macrophage production of IL-12p40. This is the first demonstration of such activity for TDM of *M. tuberculosis*.

Currently, there are two hypotheses concerning IL-12p40 production by macrophages infected with *M. tuberculosis*: either *M. tuberculosis* actively represses IL-12p40 production (Hickman et al., 2002; Nau et al., 2002) or, alternatively, *M. tuberculosis* lacks the ability to stimulate macrophage IL-12p40 production. Prior to this work, it was unclear which of these two mechanisms was at play, since the determinant from a mutant that represses IL-12p40 had not been isolated. This work provides the previously missing evidence to explain this underappreciated aspect of the immune evasion function of *M. tuberculosis*. These studies support the view that *M. tuberculosis* actively represses IL-12p40 in macrophages, and refute the idea that the lack of IL-12p40 production by macrophages infected with *M. tuberculosis* is a passive process. Further, it is suggested that deliberate repression of IL-12p40 by *M. tuberculosis* through mycolic acid modification interferes with host protective immunity.

Mycolic acids comprise ~30% of the dry weight of the tubercle bacterium (Takaya et al., 2005). The genes involved in the addition of functional groups to the mycolic acid meromycolate chains encode cyclopropane synthases (pcaA, cmaA2) and methyl transferases (mmaA1, mmaA2, mmaA3, and mmaA4). These genes are 50% to 70% identical and are thought to be S-adenosylmethione-dependent methyl transferases (Takayama et al., 2005). The three classes of mycolic acids are esterified individually to the disaccharide trehalose, producing many types of TDM, which is secreted into the cytoplasm of infected macrophages and is thought to mediate many of the cellular processes of the immune response (Rhoades et al., 2003; Karakousis et al., 2004; Geisel et al., 2005). The contribution of these functional groups of mycolic acid to the cytokine-inducing activity of TDM is beginning to be clarified. For example, loss of transcyclopropanation on oxygenated mycolic acids from the TDM purified from the ΔcmaA2 mutant causes increased TNF-α production, resulting in hypervirulence (Rao et al., 2006). On the other hand, TDM that lacks a majority of alpha mycolates from a ΔpcaA mutant causes delayed cytokine production, leading to decreased tissue destruction and increased survival of the mouse (Rao et al., 2005).

Previously, the mmaA4 gene (also known as hma) was shown to be required for the synthesis of oxygenated mycolates; however, TDM isolated from the ΔmmaA4 mutant has not previously been characterized (Dinadayala et al., 2003; Dubnau et al., 2000). Here, the finding that the ΔmmaA4 mutant does not synthesize oxygenated mycolic acids was reproduced, and it was further demonstrated that TDM devoid of oxygenated mycolic acids purified from the mutant induced increased IL-12p40 and TNF-α production over that of wtTDM. Previous work has suggested a dependence of IL-12p40 expression on TNF-α (Zhan and Cheers, 2008). Additionally, it was demonstrated that wtTDM represses both E. coli LPS and ΔmmaA4 TDM-induced IL-12p40 production. The repression observed in this experiment was specific for IL-12p40 induced by ΔmmaA4 TDM; for IL-12p40 induced by LPS, a small but significant repression was also observed for TNF-α. This observation could be explained by the hypothesis that ΔmmaA4 TDM and LPS activate different signaling pathways. This new function identified for wtTDM is a novel immunoregulatory activity.

Although wtTDM represses IL-12p40 production in the presence of agonist, it is not a classical repressor in the sense that wtTDM alone stimulates weak IL-12p40 production. One hypothesis for how wtTDM exerts both a modest stimulating and a strong inhibitory function is that wtTDM may stimulate weakly via one receptor and inhibit strongly through another. It is possible that TDM devoid of oxygenated mycolates (ΔmmaA4TDM) preferentially binds and activates a different receptor than wtTDM does. Similar observations have been made for another antagonist of E. coli LPS, penta-acylated LPS from P. gingivalis. The penta-acylated LPS from P. gingivalis weakly stimulates macrophages through toll-like receptor (TLR) 2 signaling; however, it also strongly inhibits cytokine production induced by E. coli LPS by interfering with TLR4 recognition (Darveau et al., 2004). wtTDM signaling is dependent on MYD88, an adaptor molecule for the TLR signaling pathway, but is independent of TLR2 or TLR4 receptors (Geisel et al., 2005). Therefore, wtTDM may repress IL-12p40 production by a different mechanism than does P. gingivalis LPS.

Although it cannot be distinguished which mycolic acids from the mutant, alpha or epoxy, are mediating the increase in IL-12p40 and TNF-α production, it can be concluded that the loss of oxygenated mycolates contributed to the ΔmmaA4TDM cytokine-inducing activity. An insight into ΔmmaA4TDM's stimulatory activity can be found in the functional groups on the mycolates. The polarity of each functional group relative to one another, as determined by thin-layer chromatography of mycolic acids developed in hexane/ethyl acetate solvents, showed the cyclopropane group on alpha mycolates to be apolar. The methoxy group on methoxy mycolates demonstrates intermediate polarity, whereas the carbonyl group on keto mycolates is the most polar of these functional groups. Indeed, surface pressure measurements of a Langmuir monolayer of mycolic acids showed that the polarity of each functional group contributes to the physical properties of the mycolic acids. The apolar alpha mycolates are flexible, while the keto mycolates are very rigid and the methoxy mycolates have intermediate flexibility (Villeneuve et al., 2005; Hasegawa and Leblanc, 2003). It is postulated that the flexibility of alpha mycolates allows them to adopt an array of conformations and that this may confer activating properties not observed for the oxygenated mycolates. Since the epoxy functional group is a very reactive functional group, it can be speculated that this group could also contribute to the stimulating activity of ΔmmaA4TDM.

Since IL-12p40 is a cytokine that is critical in initiating adaptive immune responses in vivo, it is predicted that the removal of inhibitors of IL-12p40 production would lead to decreased bacterial burden and increased host survival. Indeed, Dubnau et al. (2000) has shown attenuation of growth of the ΔmmaA4 mutant in a mouse model of M. tuberculosis infection. The data showing that purified ΔmmaA4TDM induced more IL-12p40 than did wtTDM provides a possible explanation of the attenuated phenotype. It is proposed that activation of host immunity by ΔmmaA4TDM results in decreased bacterial burden. It is plausible that M. tuberculosis remodels its mycolic acid composition in response to the host environment, possibly as a mechanism to repress and evade host immunity. Analysis of mycolic acid production during infection showed that M. tuberculosis synthesizes more keto mycolates following macrophage infection (Yuan et al., 1998). Additionally, the transcriptional profiling of M. tuberculosis transcripts in the lungs of infected mice showed that the mmaA4 gene is upregulated in granulomas, as compared to its growth in liquid (Rachman et al., 2006).

Microbes express species-specific molecular structures called pathogen-associated molecular patterns (PAMPs). These are recognized by macrophages, resulting in expression of cytokines and activation of host immunity (Iwasaka and Medzhitov, 2004; Kopp and Medzhitov, 2003). A prominent theme emerging from our current work with TDM, and from previous work on other mycobacterial glycolipids (Dao et al., 2004; Reed et al., 2004; Quesniaux et al., 2004; Yoshida and Koide, 1997), is that of PAMPs that normally induce protective host cytokine production into PAMPs that suppress cytokine production may be an active strategy used by pathogens to evade host immune responses. For example, studies of the purified precursor glycolipid lipomannan showed that modification of this glycolipid with arabinose generates lipoarabinomannin, which represses IL-12p40 production (Nigou et al., 2001). Phenolic glycolipid, which consists of a base structure of phenol and phthiocerol dimycocerosates, represses production of chemokines and other inflammatory cytokines. Removal of this phenol group in mutants lacking the pks 1-15 gene cluster is sufficient to reverse this repression and leads to increased mouse survival (Reed et al., 2004). It is unclear whether the host environment is involved in the temporal and spatial expression of these M. tuberculosis genes.

This paradigm of modifying PAMPs to evade host immunity is a strategy common among opportunistic bacteria that cause chronic infection (Dixon and Darveau, 2005; Miller et al., 2005; Munford and Varley, 2006). For example, P. aerugi-

*nosa* (associated with cystic fibrosis), *H. pylori* (associated with peptic ulcer disease), and *P. gingivitis* (associated with periodontal disease), have naturally occurring variants of LPS structures that antagonize cytokine production (Coate et al., 2003; Hajjar et al., 2002; Miller et al., 2005). Since colonization of *H. pylori* is dependent on flagellar-based motility, the flagellin is also modified to evade detection by the immune system (Andersen-Nissen et al., 2005; Gewirtz et al., 2004). Ultimately, all of these modifications affect the production of cytokines by the immune system, further emphasizing the importance of cytokines on the development of protective immunity.

Previous studies have shown that IL-12p70 (composed of the p40 and p35 subunits) therapy in mice infected with *M. tuberculosis* or *M. avium* decreases bacterial burden and prolongs survival (Flynn et al., 1995; Doherty and Sher, 1998; Ehlers et al., 2005; Holscher, 2004). Moreover, IL-12 therapy is a successful adjuvant to a standard drug treatment in a patient suffering from disseminated TB (Greinert et al., 2001). IL-12p70 is required for the maintenance of memory T-cells generated after *M. tuberculosis* infection (Feng et al., 2005). IL-12p40 homodimers are required for dendritic cell migration to the lymphoid organs and for activation of naïve T-cells following *M. tuberculosis* infection. Additionally, the importance of IL-12p40 homodimers in inducing protective immunity was shown by Holscher et al. (2001), who demonstrated that IL-12p40 homodimer therapy is sufficient to extend the survival of mice infected with *M. tuberculosis*. It is likely that the components involved in IL-12p40 repression have not all been identified, and the screening approach described here makes it feasible to analyze a library of *M. tuberculosis* mutants to saturation in order to identify additional components that repress IL-12p40 in virulent *M. tuberculosis*. This approach may ultimately lead to the construction of more immunogenic organisms that can be further modified to create new and more effective attenuated vaccine strains.

Materials and Methods

Reagents. Cultures of mycobacteria were routinely grown in 7H9-C media which contained Middlebrook 7H9 media supplemented with OADC (oleic acid/albumin/dextrose/catalase) (Difco, Becton-Dickinson), 0.5% Glycerol, and 0.05% Tween-80.

Morphology Studies.

Colonial phenotype for wildtype *M. tuberculosis* were observed by plating bacterial cultures on Middlebrook 7H10 plates supplemented with OADC, 0.5% glycerol, and 0.05% Tween-80. The phenotype for the ΔmmaA4 mutant was determined by plating on the 7H10 plates described above with 50 μg/ml hygromycin.

Differentiation of Bone Marrow-Derived Macrophages from BALB/c Mice.

Six-to-eight-week-old female BALB/c mice were purchased from Jackson Laboratory (Bar Harbor, Me.). Bone marrow-derived macrophages were derived from these animals, as previously described (Johnson, et al., 1983). Briefly, bone marrow cells were removed from the femurs of mice and cultured in DMEM-C containing 20% L929 cell-conditioned medium (as a source of M-CSF), for 7 days at 37° C., 5% $CO_2$. Bone marrow-derived macrophages were harvested on day 6 to plate for infection with different *M. tuberculosis* strains on day 7.

Construction of a GFP based reporter for IL-12p40 expression. The construction of the −350+55 IL-12p40-GFP Raw 294 reporter line was described previously (Dao et al., 2004). Using a similar strategy to monitor IL-12p40 expression from a full-length (FL) IL12p40 promoter (Murphy et al., 1995), position −800 to +55 relative to the transcription start of IL-12p40 promoter was amplified from C57B6 mouse genomic DNA by PCR by using upstream primer 5' ACAGGATTGCACACCTCTTTG 3' (SEQ ID NO:3) and downstream primer 5' TTGCTTTGCTGCGAGC 3' (SEQ ID NO:4). The 856 by PCR product was placed into the TOPO cloning vector (Invitrogen), giving rise to the pFL.IL12p40.TOPO vector. The full-length IL12p40 GFP reporter construct (pFL.IL-12p40.EGFP-1) was generated by removing the HindIII/PstI fragment from the pFL.IL-12p40.TOPO vector and cloned into the HindIII/PstI site of the green fluorescent protein (GFP) reporter vector, pEGFP-1 (BD Bioscience). A stable FL.IL-12p40.GFP reporter macrophage cell line was made in a mouse Raw 294.7 macrophage line. The reporter strain was grown in DMEM media with high glucose, supplemented with 10% fetal bovine serum and 10 mM Hepes, and selected with 1 mg/ml of G418, a concentration which was determined to kill Raw 264.7 cells with 99% efficiency.

Growth of *M. tuberculosis* Strains for Infection.

For each infection, a new vial of bacterial culture was brought up from stock kept at −70° C. Thawed *M. tuberculosis* H37Rv, Beijing HN878, or *M. smegmatis* was grown in 10 ml 7H9-C media, as described above. The ΔmmaA4 mutant was grown in 7H9-C media along with a selectable drug, 50 μg/ml hygromycin, while the complemented ΔmmaA4 mutant was grown in 7H9-C media under selection with 40 μg/ml of kanamycin. All mycobacterial strains were grown to an optical density of $OD_{600\ nm}$ between 0.1 to 0.3 prior to infection since mycobacterial cultures grown to OD≥0.5 undergo autolysis (data not shown) (Tullius et al., 2001). Prior to infection, the bacteria were pelleted to remove the supernatant and resuspended in 7H9-C media without drug. The resuspended pellets were sonicated 1× continuously for 10 sec.

Infection of Bone Marrow-Derived Macrophages or FL.IL-12p40-GFP Macrophage Reporter Cell Line with Mycobacteria.

Bone marrow-derived macrophages were seeded in triplicate at $2\times10^5$ macrophages per 48 well, or in 98 well for the FL.IL-12p40-GFP macrophage reporter cell line. The macrophages were infected with mycobacteria at a multiplicity of infection (MOI) of 3 or 10. After 4 hr incubation in a humidified incubator at 37° C. in the presence of 5% $CO_2$, non-ingested bacteria were removed by washing gently (three times) with pre-warmed DMEM-C cell media. Each well then received 200λ DMEM-C cell media containing 50 ug/ml gentamycin (to kill the remaining extracellular bacteria), and plates were cultured in a humidified incubator at 37° C. in the presence of 5% $CO_2$.

ELISA Measurement of Cytokine Production.

Infection was allowed to proceed for 16 to 24 hr before cell supernatants were harvested. For time course studies, the supernatants were collected at the additional time points of 48 and 72 hr. Supernatant was filtered with the 0.22 μm SpinX column (Costar) to remove any uningested extracellular bacteria. Cytokines in the conditioned medium were analyzed by sandwiched ELISA using the Biosource International (Camarillo, Calif.) kit for IL-12p40 and TNF-α, following the manufacturer's protocol.

Flow Cytometry.

Following infection of the FL.IL12p40 GFP-reporter macrophage cell line with H37Rv, HN878 Beijing, and *M. smegmatis*, the experiment was allowed to proceed for 16 to 24 hr before processing the cells for FACS analysis. Mycobacteria infected cells were trypsinized, fixed with equal volume of 4% paraformaldehyde, and left at 4° C. overnight. The following day, GFP expression was ascertained by using the FACSCalibur (BD Pharmingen) with CELLQuest (BD Biosciences) and analyzed with FlowJo software (Tree Star).

Construction of Himar-1 M. tuberculosis H37Rv Mutant Library.

The Himar-1 M. tuberculosis H37Rv mutant library was generated using the Himar-1 transposon delivered by phage, pHAE159, as described previously. Briefly, the phage containing mariner transposon was propagated to high titer in MP buffer (50 mM Tris (pH 7.6), 150 mM NaCl, 10 mM $MgCl_2$, 2 mM $CaCl_2$) and used to transduce the M. tuberculosis H37Rv strain. The transductions were plated on 7H10 plates containing 50 ug/ml hygromycin, and placed at 37° C. for three weeks. Transductants were picked into 96-well plates containing 200λ of 7H9 media supplemented with OADC, 0.5% glycerol, 0.05% Tween 80, and 50 μg/ml hygromycin. A Himar-1 transposon library of M. tuberculosis H37Rv was grown to late-log phase. Aliquots of the mariner M. tuberculosis H37Rv library were made into separate 96-well plates for stocking and were diluted and grown to mid-log phase for screening.

High-Throughput Screen for M. tuberculosis Mutants that Strongly Induce IL-12p40 Production.

The IL-12 reporter strain, Raw 294.7-FL.IL12p40-GFP, was seeded at $2 \times 10^5$ per 96 well the day before infection. Screening of the mariner transposon library was done the following day. The growth of mycobacteria in the 96 well was determined by photometric measurements of cell density at optical density (OD) 590 nm using the plate reader Viktor II. Subsequently, the mutant in each well was diluted to approximately an MOI of 10 ($2 \times 10^6$ CFU) per 10 μl. An aliquot of 10 μl of bacteria from each well was used to infect the FL.IL-12p40-GFP Raw 294 macrophage reporter cell line. Infected reporter macrophages were incubated in a humidified incubator at 37° C. in the presence of 5% $CO_2$ for 4 hr. Non-ingested bacteria were removed by washing gently (three times) with pre-warmed DMEM-C cell media. Each well then received 200 μl DMEM-C cell media containing 50 μg/ml gentamycin, and the plates were cultured in a humidified incubator at 37° C. in the presence of 5% $CO_2$ for 16 hr, at which time IL-12 expression was found to be maximal. The GFP expression from individual wells on the plate was determined by the use of the Viktor II plate reader, which was set at 488 nm/530 nm excitation/emission filter pair and to a reading of 1.0 sec per well. For secondary screening of the candidates, the mutants were expanded in 10 ml cultures, and grown to an $OD_{600nm}$ of between 0.1 and 0.3. The IL-12 reporter macrophages were infected with the candidate in duplicate and incubated overnight, as described above. After 16 hr, the cells were harvested by trypsinization, and single-cell suspensions from these infected macrophages were generated. Next, an equal volume of 4% paraformaldehyde was added to each well. The cells were fixed overnight at 4° C. Flow cytometer analysis for GFP expression was performed the following day.

Construction of phagemid for deletion of mmaA3 and mmaA4. The mmaA3 (RvO643c) and mmaA4 (RvO642c) mutants were constructed by homologous recombination using the specialized transducing phages. The deleted sequence was replaced with hygromycin cassette. Construction of the mmaA3 phagemid: The deletion phagemid for the ΔmmaA3 mutant was constructed by PCR amplification of the 5'-flanking region of mmaA3 using M. tuberculosis H37Rv genomic DNA with the following primer pairs: 0643cRL 5' TTTTTTTTCCATAGATTGGTCACTCGAT-CACCGGCTTGCACGTA 3' (SEQ ID NO:5) and 0643cRR 5' TTTTTTTTCCATCTTTTGGG-GAGACGTCGTAGTGCGCTTGGATG 3' (SEQ ID NO:6). This PCR product is 553 bp. For the 3' flanking region of mmaA3, the following primer pairs were used: 0643c LL 5' TTTTTTTACCATAAATTGGGGAA-CAGTCGGCGAAGACGGGTTT 3' (SEQ ID NO:7) and 0643cLR 5' TTTTTTTTCCATTTCTTGGTGAAGTTG-GCCCAGTCGCTCAGCAG 3' (SEQ ID NO:8). This PCR product is 811 bp. Construction of the mmaA4 phagemid: The deletion phagemid for the ΔmmaA4 mutant was constructed by PCR amplification of the 5'-flanking region of mmaA4 from M. tuberculosis H37Rv genomic DNA using the primer pairs 0642cRL 5' TTTTTTTTCCATAGATTGGT-TCGAGACGGCGCGTTTCATCA 3' (SEQ ID NO:9) and 0642cRR 5' TTTTTTTTCCATCTTTTGGCGACCCGCG-TAAGGCAGACCAG 3' (SEQ ID NO:10) for the 5 prime arm. This PCR product is 994 bp. The primer pairs were 0642cLL 5' TTTTTTTACC ATAAATTGG AGC ACTC-GATC ACCGGCTTGC ACGTA 3' (SEQ ID NO:11) and 0642cLR 5' TTTTTTTTCCATTTCATGGTCCAACCG-CACCCAATGTCCAGCAG 3' (SEQ ID NO:12) for the downstream arm, which gives rise to a 723 bp PCR product.

Following cloning into p0004S (0642c.p004S or 0643c.p004S), the resulting plasmid was then packaged into the temperature-sensitive phage phAE159, as described earlier, to yield the knockout phages [ok?] for mmaA3 (phAE301) and mmaA4 (phAE302). Specialized transduction was performed, as described previously (Bardarov et al., 2002), and the transduction mix was spread on 7H10 plates, selecting with 50 μg/ml hygromycin.

Construction of ΔmmaA4 Complementing Strain.

Complementation analyses were performed with the cosmid 3E2 (Rv0630c-Rv0654c), which contains the mmaA4 gene in the integration proficient vector pYUB412. The transformation of the mutant strains with the constructs was described previously. Kanamycin-resistant clones were screened for reversion of mutant colonial morphology.

Small-Scale Lipid Extraction and MAME Analysis.

Initially, 10 ml cultures of wildtype M. tuberculosis, ΔmmaA4 mutant, or complemented ΔmmaA4 mutant at an $OD_{600\ nm}$~0.4 were labeled using 1 μCi/ml [$^{14}$C]-acetic acid and further incubated for 12 hr. Cells were recovered by centrifugation at 27,000×g for 10 min and carefully freeze-dried using a Savant SpeedVac. Cellular-associated lipids were extracted twice using 2 ml of $CHCl_3/CH_3OH/H_2O$ (10:10:3, v/v/v) for 3 hr at 50° C. Organic extracts were combined with 1.75 ml $CHCl_3$ and 0.75 ml $H_2O$, mixed, and centrifuged. The lower organic phase was recovered, backwashed twice with 2 ml of $CHCl_3/CH_3OH/H_2O$ (3:47:48, v/v/v), and then dried and resuspended with 200 μl of $CHCl_3/CH_3OH$ (2:1, v/v). The residual cell pellet was subjected to alkaline hydrolysis using 15% aqueous tetrabutylammonium hydroxide (TBAH) at 100° C. overnight, followed by the addition of 4 ml of dichloromethane, 300 ml iodomethane, and 4 ml of water. The entire reaction mixture was then mixed for 1 hr. The upper aqueous phase was discarded and the lower organic phase washed twice with water and evaporated to dryness. Mycolic acid methyl esters (MAMES) were re-dissolved in diethyl ether. After centrifugation, the clear supernatant was again dried and resuspended in dichloromethane (100 ml) and an aliquot subjected to 1D-High Performance Thin-Layer Chromatography (1D-HPTLC), using two developments of hexane/ethyl acetate [95:5]). MAMES were visualized by autoradiography by exposure of TLCs to X-ray film (Kodak X-Omat).

Large-Scale Lipid Extraction and Purification of TDM.

Four liter cultures of wildtype M. tuberculosis or ΔmmaA4 mutant were grown to $OD_{600nm}$=0.4. Mycobacteria were recovered by spinning at 3000 RPM for 15 min on a table-top centrifuge. Cellular lipids were extracted as described above from freeze-dried cells twice using 200 ml of $CHCl_3$/$CH_3OH$/$H_2O$ (10:10:3, v/v/v) for 3 hr at 50° C. Organic extracts were combined with 175 ml $CHCl_3$ and 75 ml $H_2O$, mixed, and centrifuged. The lower organic phase was recovered, back washed twice with 200 ml of $CHCl_3$/$CH_3OH$/$H_2O$ (3:47:48, v/v/v), dried, and resuspended with 2 ml of $CHCl_3$/$CH_3OH$ (2:1, v/v). The lipid extract was examined by two-dimensional TLC on aluminum-backed plates of silica gel 60 E254 (Merck 5554, city/state), using chloroform/methanol/water (100:14:0.8, v/v/v) in the first direction and chloroform/acetone/methanol/water (50:60:2.5:3, v/v/v) in the second direction. TDM was visualized either by spraying plates with α-naphthol/sulfuric acid, or by spraying with 5% ethanolic molybdophosphoric acid followed by gentle charring.

The crude lipid extract (250 mg) dissolved in chloroform/methanol (2:1, v/v) was applied to a diethylaminoethyl (DEAE) cellulose column (2 cm×15 cm) and the flow-through kept for further purification. TDM was further purified by preparative TLC on 10 cm×20 cm plastic-backed TLC plates of silica gel 60 F254 (Merck 5735, Darmstadt, Germany), run in chloroform/methanol/ammonium hydroxide (80:20:2, v/v/v). The plates were then sprayed with 0.01% 1,6-diphenyl-1,3,5-hexatriene dissolved in petroleum ether/acetone (9:1 v/v), and lipids were visualized under UV light. Following detection, the plates were re-developed in toluene to remove diphenyl-1,3,5-hexatriene and the corresponding TDM band scraped from the plates and extracted from the silica gel using three extractions of chloroform/methanol (2:1, v/v) to provide highly purified TDM.

The highly purified TDM from wildtype *M. tuberculosis* was reconstituted in petroleum at a concentration of 200 μg/ml. Aliquots of 500 μl were made into endotoxin-free glass vials, and the samples were dried under nitrogen for storage. The TDM stock was tested for endotoxin contamination using the Limulus Amoebocyte Lysate (LAL) assay from Bio Whittaker, following the manufacturer's protocol. Briefly, TDM in one of the vials was resuspended in DMSO to a $C_f$=1 mg/ml. 10 μl of the sample was used in the LAL assay. The TDMs from wildtype *M. tuberculosis* H37Rv or ΔmmaA4 mutant were endotoxin-free (data not shown).

Reconstitution and Dilution of TDM for Macrophage Stimulation.

At the time of the experiment, 100 μg TDM was reconstituted to 100 μg/500 μl with petroleum ether. A series of 2-fold dilutions of TDM was made with petroleum ether to yield 10 μg/100 μl, 5 μg/100 μl, and 2.5 ug/100 4 after which 100 μl was used to coat a 48-well plate. The plate was air dried to evaporate the solvent and washed once with PBS, then air dried again. The TDM dose used in this assay is higher than that used for PAMPs from gram-negative bacteria, such as lipopolysaccharide, but comparable to that of PAMPs from gram-positive bacteria, such as lipoteichoic acid and peptidoglycan (Ellingsen et al., 2002; Takeuchi et al., 1999; Grangette et al., 2005). Bone marrow-derived macrophages were then immediately added at $2\times10^5$ cells/200 μl per well. For TDM and ΔmmaA4TDM cotreatment, 10 μg/100 μl wtTDM and 5 μg/100 μl mmaA4TDM were individually added to a 48-wells plate. The contents were mixed to ensure even distribution of the lipids before the plate was air-dried, washed with PBS, then air dried again before the addition of macrophages. For *E. coli* LPS and wtTDM cotreatment, the wells were first coated with 2.5 ug wtTDM, air dried, washed with PBS, then aired dried again; this was followed by the layering of bone marrow-derived macrophages and the addition of 100 ng/ml *E. coli* LPS. Cell supernatants were harvested, filtered, and then analyzed by ELISA, as described above.

Example 2

Sterilizing Immunity Elicited Against
*Mycobacterium tuberculosis* in Mice Following
Immunization with an *M. smegmatis* Lacking Genes
Encoding Immune Killing Evasion Functions Example Summary In the evolution of the *Mycobacterium* genus, mycobacterial cells evolved ways to evade killing by phagocytic cells. Described here is a set of genes, the ike locus, for immune killing evasion, which when deleted from *M. smegmatis* allow the resulting mutant to be readily killed in mouse lungs by the innate immune system. The killing of this mutant correlates with the induction of high levels of IL-12p40, IL-12p70, and IFN-γ. Vaccination of immunocompetent mice with *M. smegmatis* Δike or *M. smegmatis* Δike containing the *M. tuberculosis* ike region conferred significant protection to mice challenged intravenously with a high dose of *M. tuberculosis*. Whereas naïve mice die in 7 to 10 days following challenge, the mice immunized with *M. smegmatis* Δike survived 40 to 50 days and 60% of the mice immunized with *M. smegmatis* Δike containing *M. tuberculosis* ike greater than 70 days. Analysis of the mouse lung of one of the surviving mice revealed no detectable *M. tuberculosis* infection and the other 2 mice at day 85 post challenge appear to be fully healthy and gaining weight. This data suggests that the vaccination has elicited effective sterilizing immunity. It is hypothesed that the *M. smegmatis* Δike mutant elicits a robust TH1 response by virtue of its IL-12 inducing abilities and pro-apoptotic phenotypes. Thus, the *M. smegmatis* Δike mutant appears to be an attractive vaccine vector to develop TH1 type immunity.

Introduction

Region 3 (R3), one of the homologs to RD1, from *M. tuberculosis* was annotated as essential by Sassetti et. al. (2001), and certain genes within this region were found to be up-regulated upon infection of mouse lungs. Since this region is the most conserved in all of the mycobacterial species, we hypothesized that Region 3 from *M. tuberculosis* plays some essential function in immune evasion.

Results

Construction of RD1 Homologue and Paralogue Deletion Mutants of *M. smegmatis*.

Figure 7:
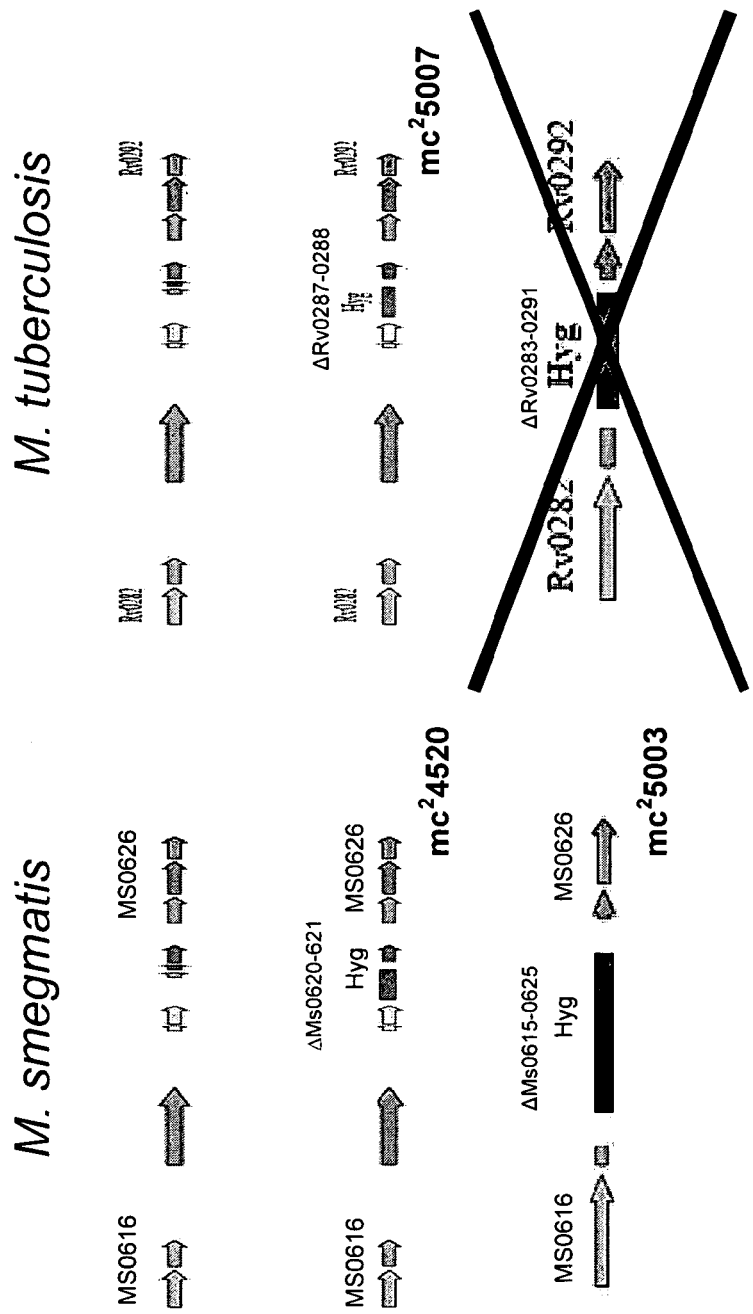
FIG. 7 is diagrams of genetic constructs for insertion into *Mycobacterium smegmatis* and *M. tuberculosis*. The "X" through the bottom diagram of the *M. tuberculosis* constructs indicates the *M. tuberculosis* transduced with that construct could not be established, indicating Region 3 is essential in *M. tuberculosis*.

Using specialized transduction, the esat-6/cfp-3-10 like proteins were deleted from region 1 (R1), as well as their paralogs in regions 3 and 4. The entire region 1 secretion system was also identified, including genes Msmeg0615 through Msmeg0626, as well as the entire region 3 and 4 secretion systems. Regions 2 and 5, which are present in *M. tuberculosis*, have no homologs in *M. smegmatis*. Thus it was determined that neither the esat-6/cfp-10 genes nor the entire secretion system for these genes are essential in *M. smegmatis*. The same deletions were attempted in *M. tuberculosis*, and similar results were obtained with one exception. A deletion of the entire Region 3 esat-6/cfp-10 like secretion system could not be generated in *M. tuberculosis*, even though the esat-6/cfp-10 like genes were able to be deleted separately. Thus Region 3 plays some essential role in *M. tuberculosis*. FIG. 7 shows a summary of the constructs used to make the subject mutations.

Unlike *M. smegmatis* ΔR1 and ΔR4, the *M. smegmatis* ΔR3 Fails to Kill immunocompetent or immunocompromised mice.

Figure 8C:
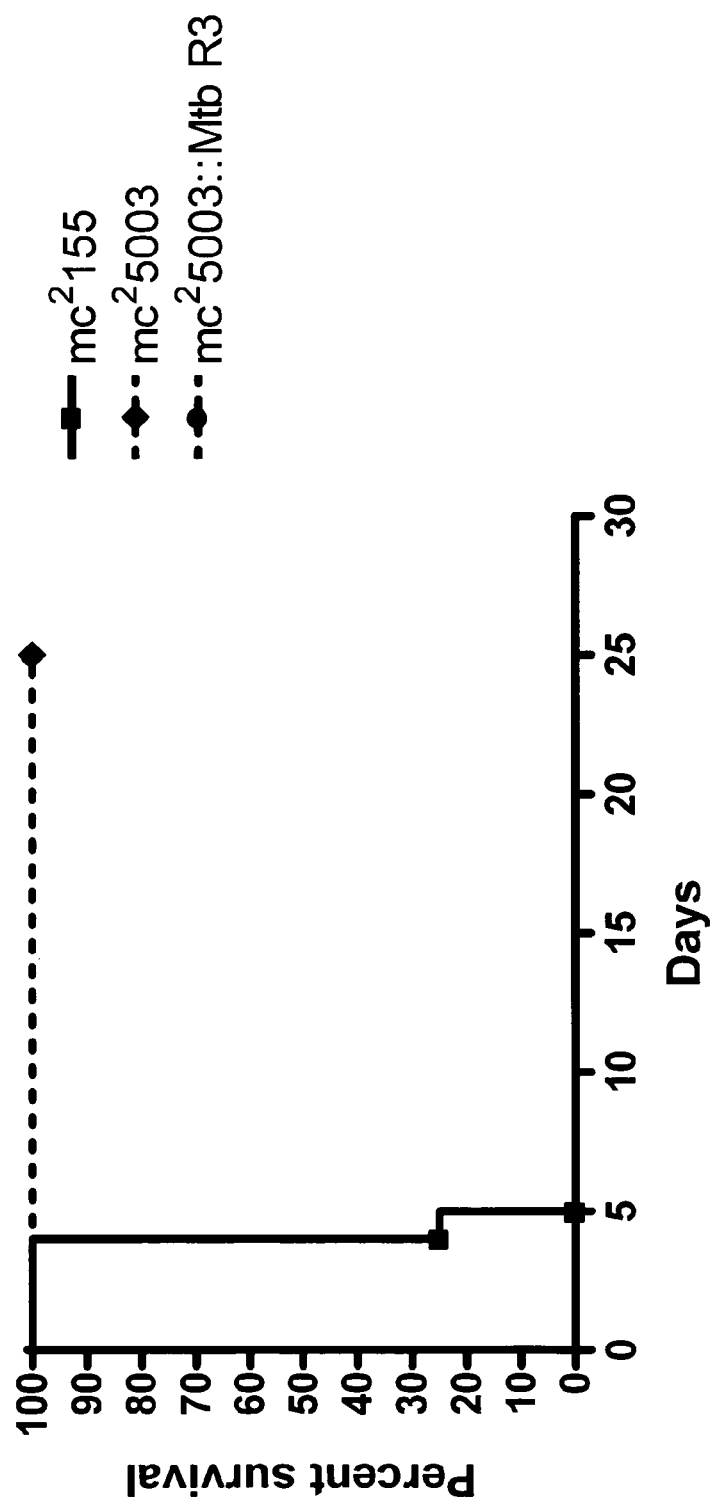
FIG. 8 is graphs showing survival of C571B1/6 (Panel A), SCID (Panel B), and Rag−/− (Panel C) mice inoculated with $5\times10^7$ cells of various *M. smegmatis* strains. Wild-type (mc$^2$1.55) and the region 1 deletion in *M. smegmatis* (mc$^2$5001) both kill immunocompromised and immunocompetent mice, whereas the region 3 deletion in *M. smegmatis* mc$^2$5003; i.e. Δ(Ms0615-Ms0626)) does not. In addition, inoculation of the mc$^2$5004 strain containing the genes for region 3 *M. tuberculosis* (mc$^2$5003::Mtb R3) at the same dose does not kill immunocompetent or immunocompromised mice.

Intravenous infections of C57B1/6 mice with $10^6$ *M. smegmatis* $mc^2155$ have previously been shown to be rapidly cleared from these mice. The bacteria do not persist in the mouse, nor does it cause mortality of the mice. Increasing the dose to $10^7$ *M. smegmatis* $mc^2155$ or higher induces mortality of the mice within 7 days. Infection of immunocompromised SCID or Rag–/– mice show the same phenotype. When the *M. smegmatis* ΔR1, ΔR3, and ΔR4 strains were also tested for virulence by administration of a $5×10^7$ cells IV, only strains ΔR1 and ΔR4 achieved mortality of C57B1/6 mice (FIG. 8A). Further, the *M. smegmatis* ΔR3 strain failed to kill immunocompromised SCID or Rag–/– mice (FIGS. 8B and C). This suggests that the *M. smegmatis* ΔR3 strain is highly attenuated in mice.

The R3 Region of *M. smegmatis* Provides an Immune Killing Evasion Function and is Readily Killed in Mouse Lungs.

Figure 9:
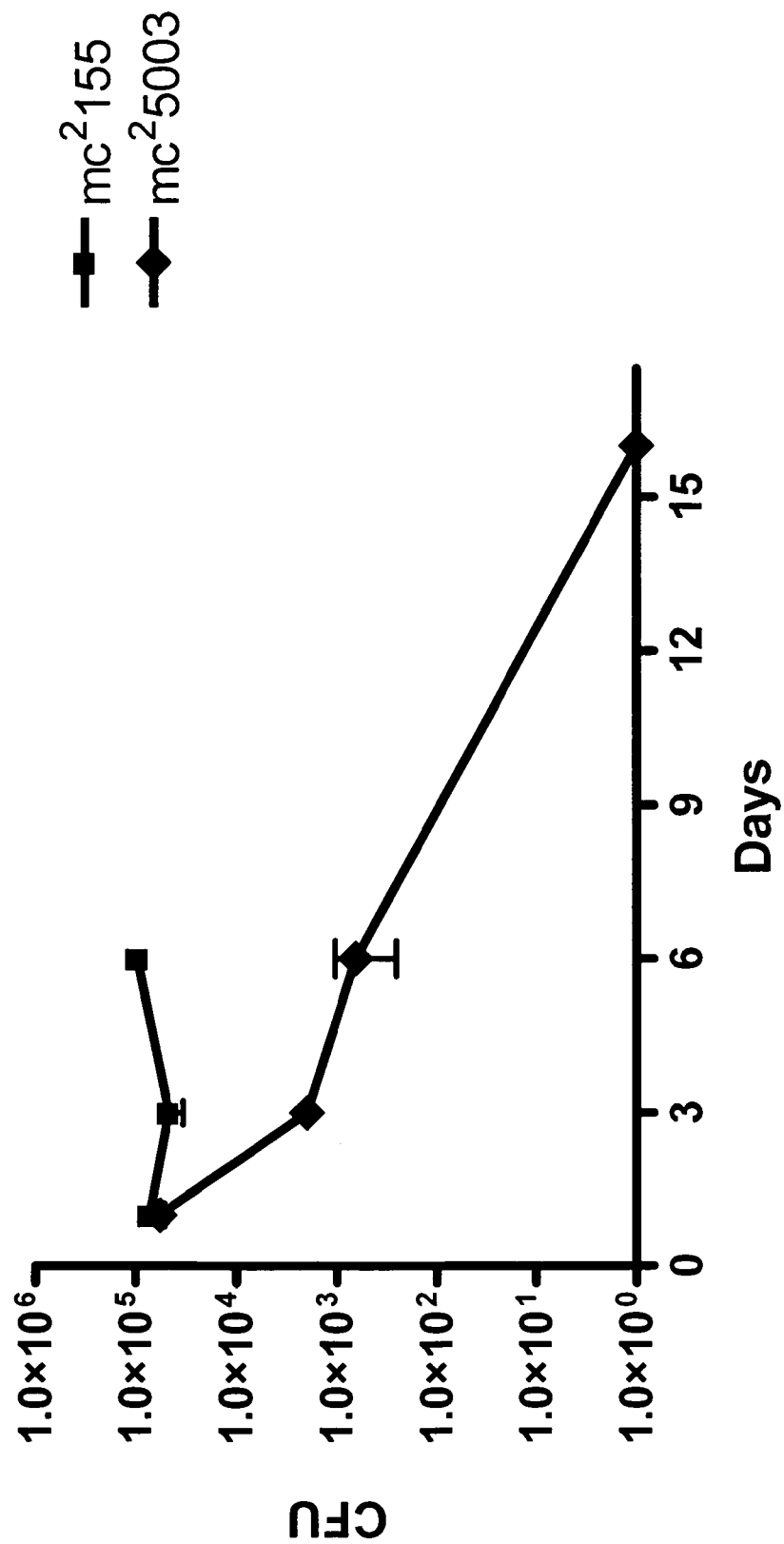
FIG. 9 is a graph showing the rapid clearance of the *M. smegmatis* region 3 deletion strain vs. the maintenance of wild-type *M. smegmatis* after high dose ($5\times10^7$) inoculation.

Having observed the failure of the R3 deletion mutant to kill mice, the clearance of this strain in the organs of the infected mice was examined. Remarkably, this mutant was killed in mouse lungs in a highly efficient manner (FIG. 9). Three days post-infection showed an almost 2 log drop of bacterial CFU counts in the lung as compared to wild-type and initial infecting doses. This clearance continued, finally resulting in elimination of the R3 mutant from the lungs by day 16 post-infection. Clearance, with less rapidity than what was seen for the lungs, was observed in several other organs, namely the spleen, liver, kidneys, and brain of the infected mouse. Pathology observed from these organs confirmed the hypothesis that the R3 mutant elicited a more effective immune response as compared to wild-type *M. smegmatis*, resulting in the rapid clearance of the organism. Wild-type *M. smegmatis* infection was characterized by a persistent neutrophil infiltration, correlating with widespread tissue destruction and ultimately death. In contrast, infection with the R3 mutant was correlated with initial neutrophil infiltration, followed by a rapid replacement of that population with macrophage. It is concluded that this region must have evolved to evade immune killing functions, and so the genes which compose region 3 are hereby named ike for Immune Killing Evasion.

The *M. smegmatis* Δike Mutant Containing the *M. tuberculosis* ike Cosmid Fails to Kill Immunocompetent or Immunocompromised Mice.

Figure 10:
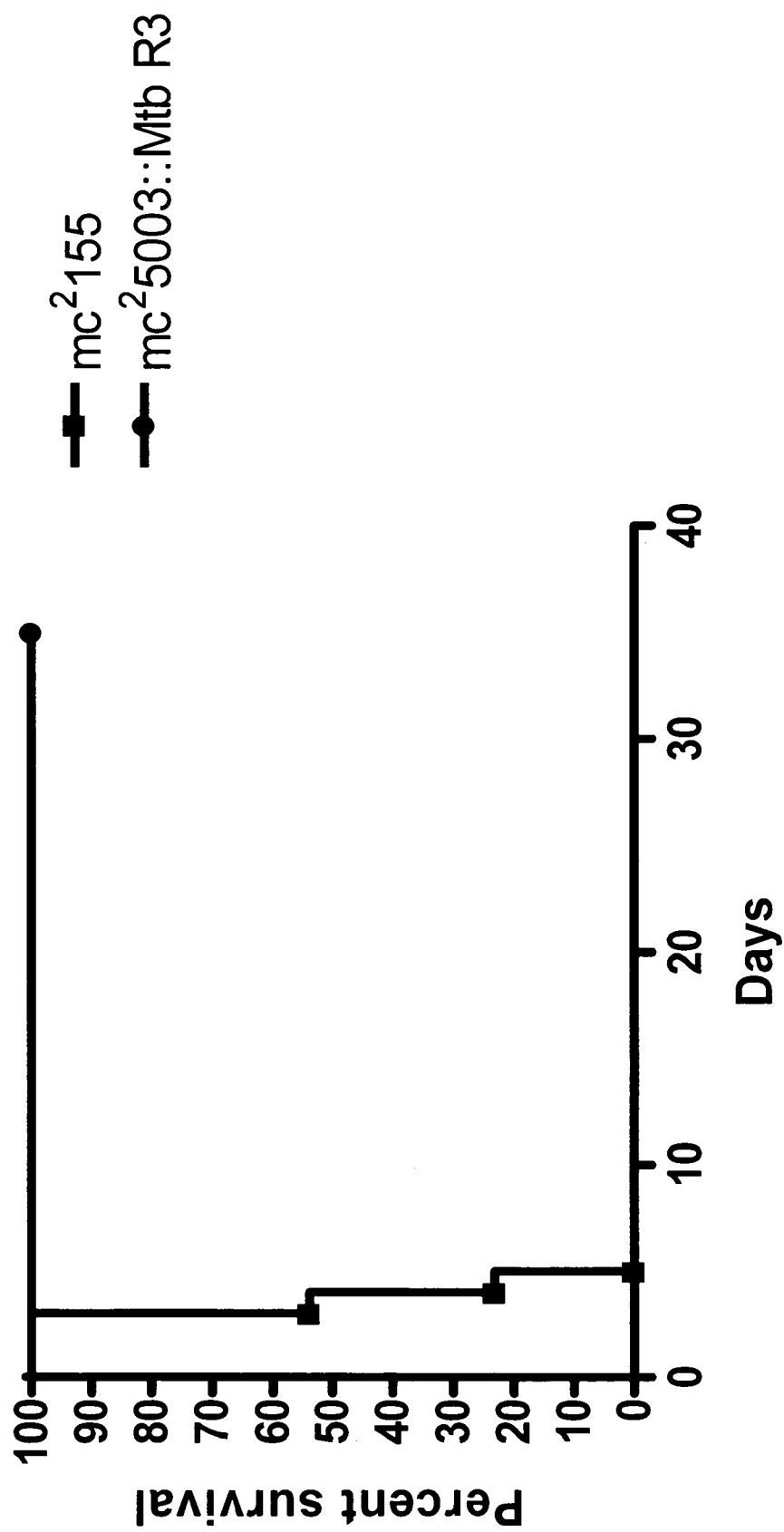
FIG. 10 is a graph showing survival of C57B1/6 mice after inoculation with $5\times10^7$ cells IV of the *M. smegmatis* region 3 deletion containing region 3 from *M. tuberculosis*, vs. wild-type *M. smegmatis* strain.

Whether Region 3 from *M. tuberculosis* could complement the Region 3 deletion from *M. smegmatis* was determined. Using an *M. tuberculosis* cosmid library, the cosmid containing the *M. tuberculosis* R3 (ike) region was determined. This was cloned into the *M. smegmatis* Δike mutant, generating the *M. smegmatis* Δike::*M. tuberculosis* ike strain. This strain was infected at a high dose intravenously into immunocompetent C57B1/6 mice, as well as immunocompromised $Rag^{-/-}$ mice. Interestingly, the *M. tuberculosis* ike did not fully complement the *M. smegmatis* Δike mutant, since the strain failed to kill C57B1/6 or $Rag^{-/-}$ mice (FIG. 10).

The *M. smegmatis* Δike Mutant as Well as the *M. smegmatis* Δike::*M. tuberculosis* ike Strain Elicits High Levels of IL-12, IFN-γ, and TNF-α in Mice Following Intravenous Infections.

Figure 11:
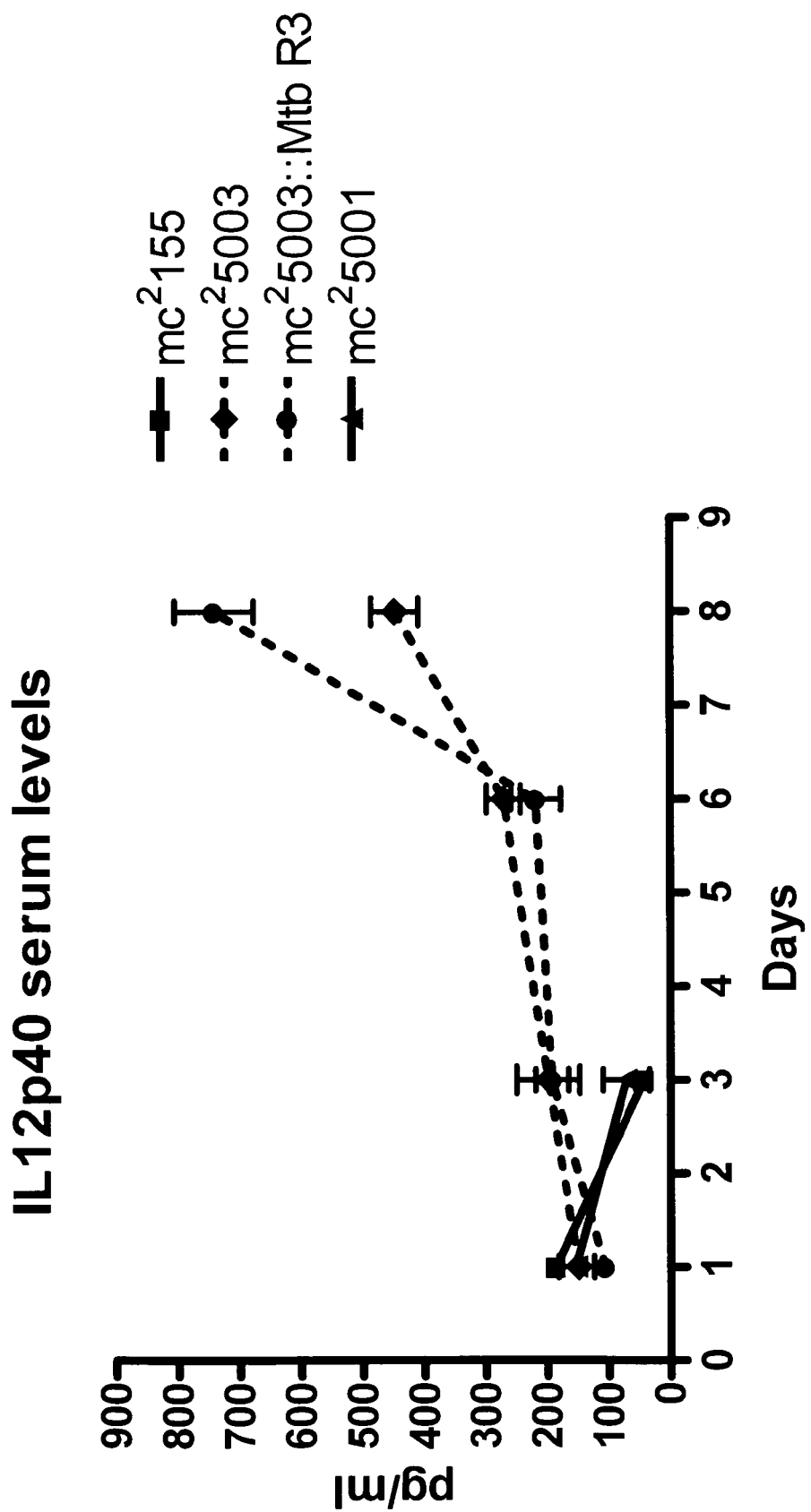
FIG. 11 is a graph showing increased serum levels of IL12p40 in mice after inoculation with both region 3 *M. smegmatis* deletion strains, or the region 1 deletion strain, vs. wild-type *M. smegmatis*.

Serum cytokine levels were measured in C57B1/6 mice over several days following infection with wild-type *M. smegmatis* and two Δike mutant strains. Levels of IL-6, IL-12, IFN-γ, and TNF-α were measured to identify whether a Th1 response was being elicited from these mice. A continual increase in serum IL-12, IFN-γ, and TNF-α levels was observed from Δike mutant infected mice, 4 to 8 fold as compared to wild type infected mice, which eventually returned back to normal levels (FIG. 11). The ΔR1 *M. smegmatis* strain infected mice exhibited the same cytokine profile as wild-type infected mice. However, the strain that had a partial deletion in the ike region, $mc^2452$ (deletion of only genes Ms0620-0621), showed no increase of IL-12 production over the wildtype strain (data not shown), indicating that those genes are not required to suppress IL-12 production. Interestingly, the *M. smegmatis* Δike::*M. tuberculosis* ike strain generated 2-fold higher serum IL-12 levels than the *M. smegmatis* Δike mutant alone. Serum cytokine levels of IL-6 increased up until death in wild-type *M. smegmatis* infected mice, whereas IL-12, IFN-γ, and TNF-α serum levels were generally undetectable. Thus, ΔR3 and ΔR1 in *M. smegmatis* seem to maintain separate functions, and the *M. smegmatis* Δike::*M. tuberculosis* ike strain appears more immunogenic.

Mice Immunized with the *M. smegmatis* Δike Mutant as Well as the *M. Smegmatis* Δike::*M. tuberculosis* ike Strain are Protected from High Dose *M. tuberculosis* Challenge.

Figure 12:
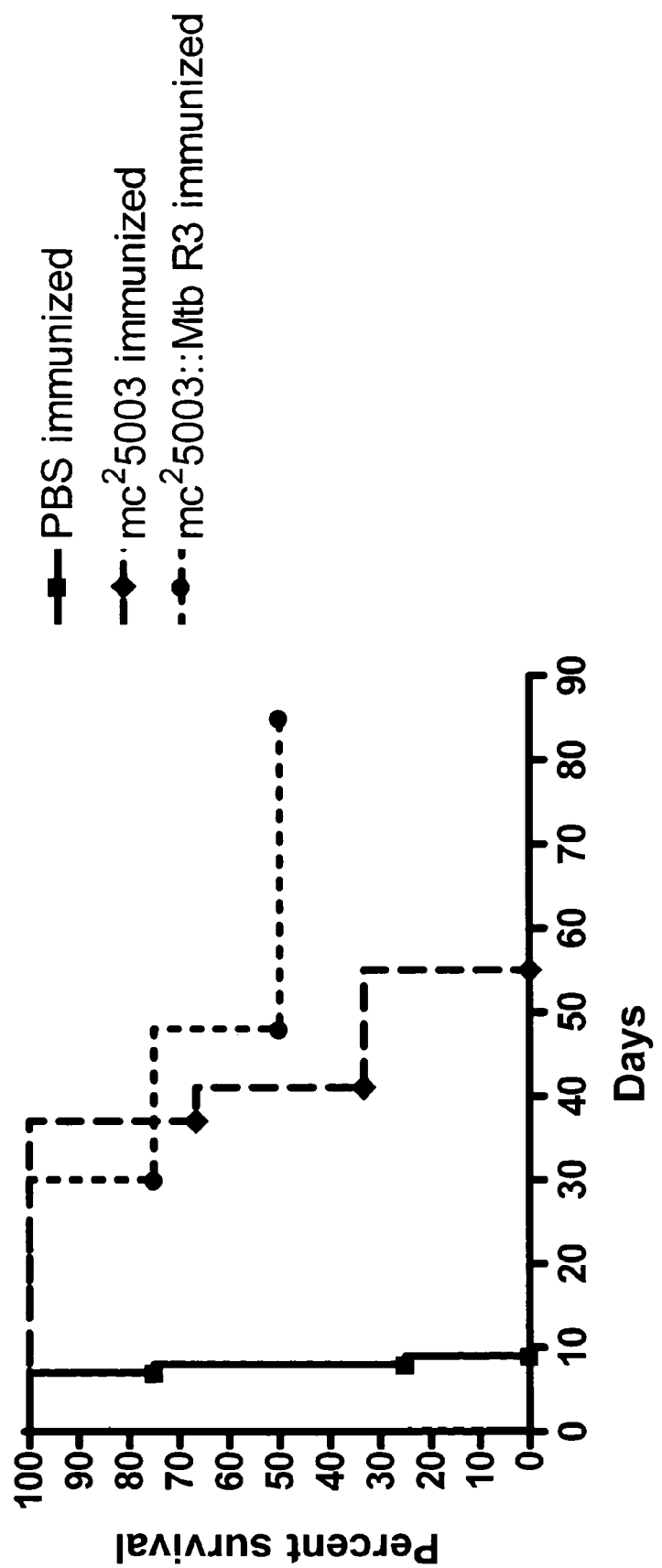
FIG. 12 is a graph showing survival of mice immunized with both region 3 *M. smegmatis* strains vs. PBS immunization as indicated, then challenged with a $10^8$ cells IV of H37Rv, a virulent *M. tuberculosis*.

Mice were immunized intravenously ($5×10^7$ cells) with the *M. smegmatis* Δike mutant as well as the *M. smegmatis* Δike::*M. tuberculosis* ike strain. After waiting five weeks for the bacteria to clear, the mice, along with a naïve control group, were subsequently challenged with a high dose ($10^8$) of the virulent *M. tuberculosis* H37Rv. The results are shown in FIG. 12. The un-immunized mice died between 7 and 10 days post-challenge. Mice previously immunized with *M. smegmatis* Δike mutant survived on average for 50 days post-challenge. The mice immunized with the *M. smegmatis* Δike::*M. tuberculosis* ike strain survived over on average 65 days post-challenge, and surprisingly, fifty percent of the mice from this group were still alive 85 days post infection. These mice appear to be fully healthy and are gaining weight. Thus, the *M. smegmatis* Δike::*M. tuberculosis* ike strain provides a protective advantage from *M. tuberculosis* challenge over the *M. smegmatis* Δike mutant alone.

The *M. smegmatis* Δike Mutant Induces More IL-12p40 In Vitro than the Wild-Type or the *M. smegmatis* Δike::*M. tuberculosis* ike Strain.

In order to determine a mechanism of killing in vivo, a macrophage IL-12p40 transcription reporter cell line was infected in vitro. This cell line contains a GFP gene fused to the IL-12p40 promoter integrated into the chromosome of the J774 cell line. This cell line was tested to ensure fidelity to the native promoter, and then used for screening purposes. Upon infection, the *M. smegmatis* Δike mutant induced 4-5 fold more IL-12 transcription than the parent wild-type strain. This induction was, complemented when the Δike region from *M. tuberculosis* was integrated into the *M. smegmatis* Δike mutant strain. This was surprising, since in vivo studies with this recombinant strain did not show complementation of the phenotype. Deletion of an un-related factor, GroE1, from the *M. smegmatis* genome did not alter IL-12p40 transcription. Furthermore, this induction is not dependent on the Esat-6/Cfp-10-like proteins in this region, since deleting them did not induce IL-12p40 transcription. Thus the repression that is being observed in the wild-type strain is a consequence of Region 3 itself or secreting some other factor.

Figure 13:
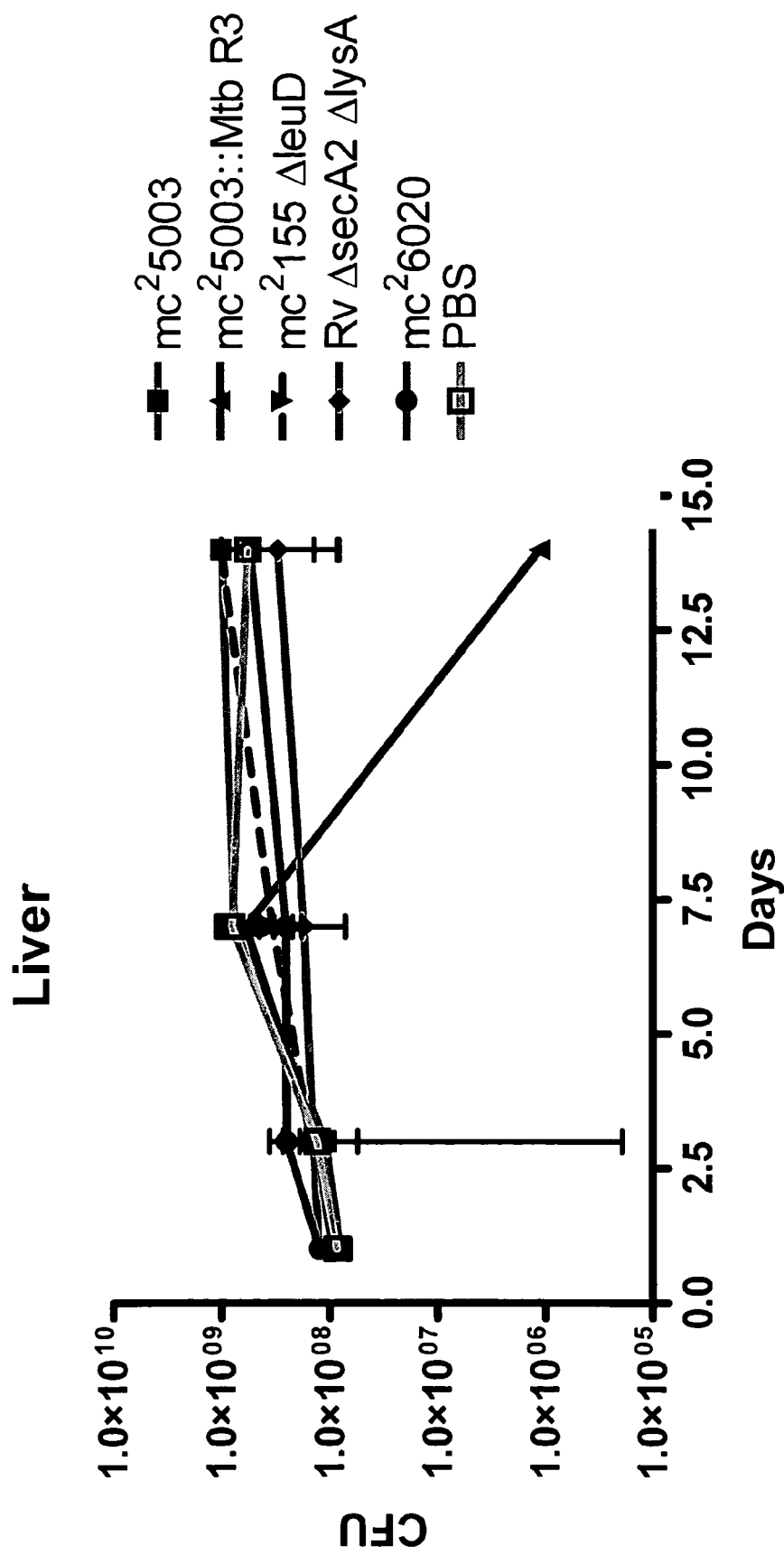
FIG. 13 is a graph showing levels of *M. tuberculosis* in the liver of mice inoculated with various *mycobacterium* strains then subsequently challenged with a virulent *M. tuberculosis*.
Figure 14:
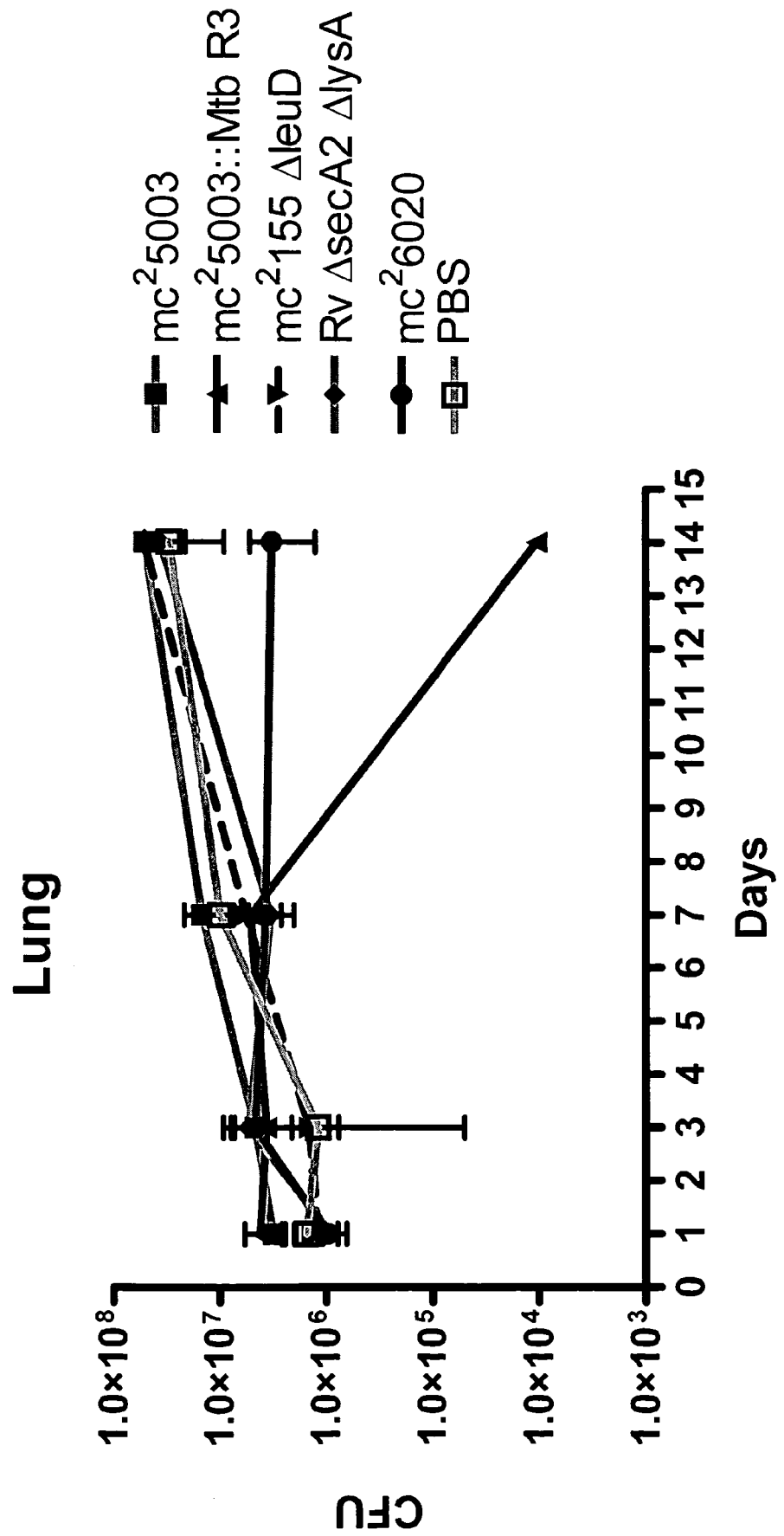
FIG. 14 is a graph showing levels of *M. tuberculosis* in the lungs of mice inoculated with various *mycobacterium* strains then subsequently challenged with a virulent *M. tuberculosis*.
Figure 15:
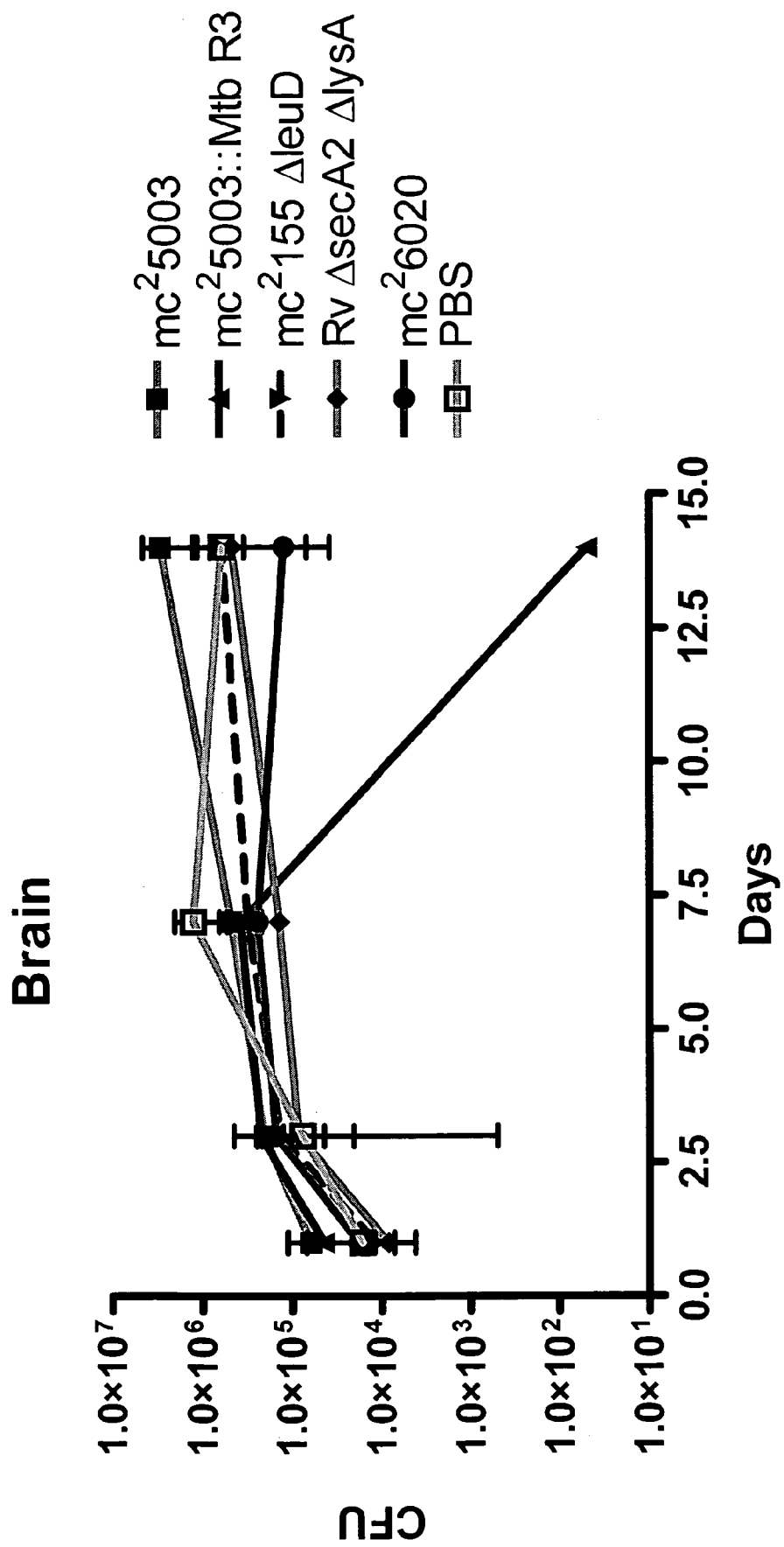
FIG. 15 is a graph showing levels of *M. tuberculosis* in the brain of mice inoculated with various *mycobacterium* strains then subsequently challenged with a virulent *M. tuberculosis*.

Mice immunized with the *M. smegmatis* Δike::*M. tuberculosis* ike strain kill wild-type *M. tuberculosis* in the lung, liver, and brain after challenge. In order to determine whether the survival of C57B1/6 mice after immunization and challenge was a result of elimination of the bacteria from the mouse organs, CFU counts were taken at various time points post-challenge. The largest difference seen between the immunization groups was between 7 and 14 days. The *M. smegmatis* Δike::*M. tuberculosis* ike strain $mc^25003$::Mtb R3 was able to successfully reduce the CFU counts in the liver 2.5 logs compared to all other immunization groups and the PBS control (FIG. 13). This reduction was also seen in the lung, 2.5 logs (FIG. 14), and the brain, 4 logs (FIG. 15). This type of sterilization has not been seen previously for any *M. tuberculosis* challenge. Our data suggests that immunization of mice with the *M. stegmatis*Δike::*M. tuberculosis* ike strain produces an adaptive immune response that is able to kill *M. tuberculosis* upon subsequent challenge.

Figure 16:
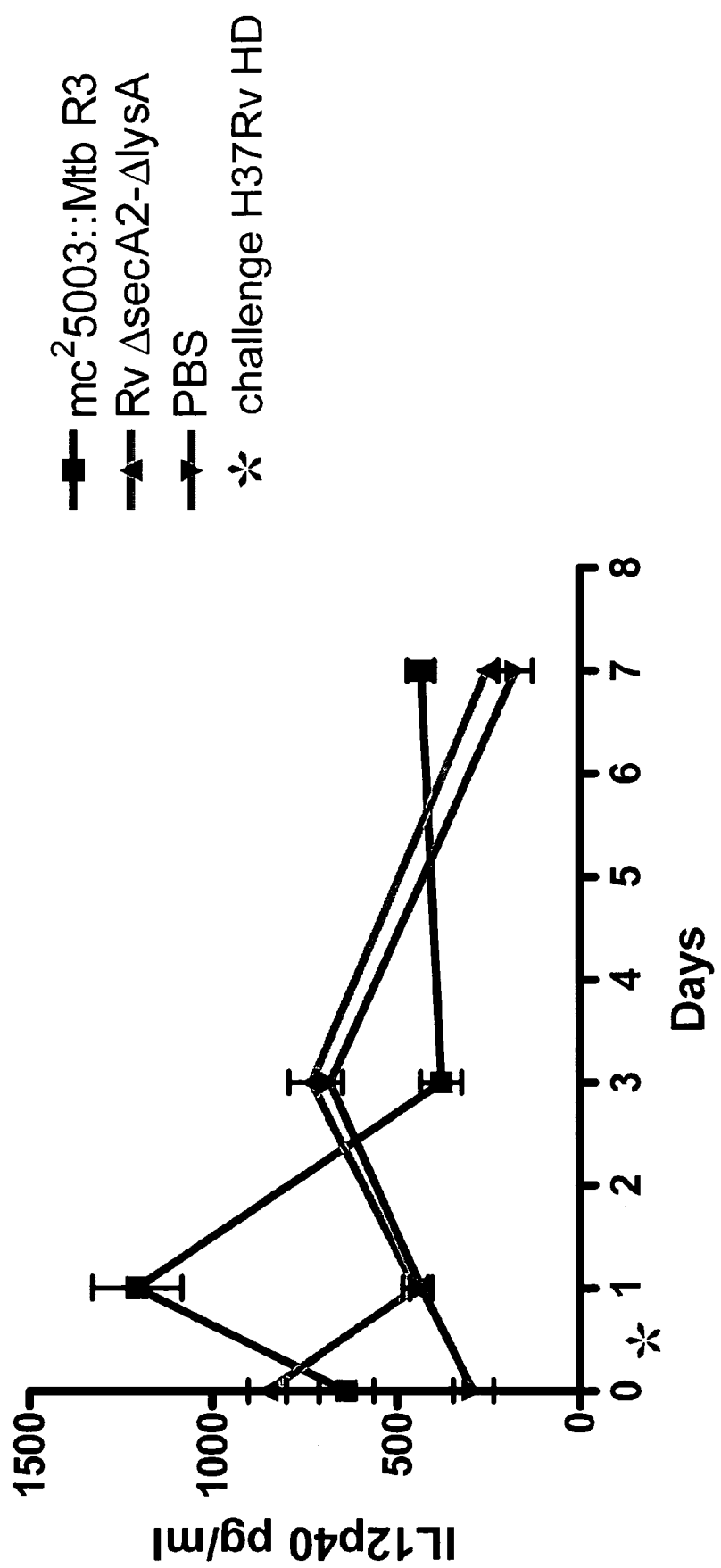
FIG. 16 is a graph showing serum concentrations of IL12p40 in mice inoculated with PBS or either of two *mycobacterium* strains, then challenged with a virulent *M. tuberculosis*.

IL12p40 serum concentrations were measured after challenge of mice inoculated with the *M. smegmatis* Δike::*M. tuberculosis* ike strain mc$^2$5003::Mtb R3 and RvΔsecA2-ΔlysA. The mice inoculated with the mc$^2$5003::Mtb R3 strain showed a large rise in IL12p40 concentrations within a day of challenge with the virulent *M. tuberculosis* strain H37Rv HD (FIG. 16).

Discussion

Deletions of esat-6/cfp-10 from R3 alone, as well as the entire region were generated in *M. smegmatis*. It was confirmed that the entire R3 deletion from *M. tuberculosis* is essential, whereas the esat-6/cfp-10 deletion is not. The R3 mutant in *M. smegmatis* upregulates IL-12 transcription, whereas the esat-6/cfp-10 deletion has no effect on IL-12 in *M. smegmatis* or *M. tuberculosis*. Further, complementation of the *M. smegmatis* R3 deletion with *M. tuberculosis* R3 restores the IL-12 suppressive phenotype. This complementation is characterized by necrosis of in vitro macrophage culture, allowing *M. smegmatis* to grow in macrophage. Infection of a high dose of wild-type *M. smegmatis* will kill C57B1/6 and SCID mice, while the R3 deletion allows for survival of these mice. Most interesting is the rapid rate of killing of the R3 deletion mutant from the mouse lungs. Serum cytokine levels parallel what is seen in vitro in that IL-12 and IFN-γ is upregulated in the R3 mutant infected mouse. Ultimately, Region 3 appears to be essential for protection from innate immune responses, and this evasion is mediated by some secreted molecule other than Esat-6 or Cfp-10.

Example 3

IKE/R3 of *M. smegmatis* Prevents Recruitment of Hrs

Brief Introduction on Cell Biology of Phagosome Maturation

Macrophages have an innate ability to engulf foreign particles, including bacteria, into intracellular compartments called phagosomes. This phagocytosis event is then followed by a series of events leading to maturation of the phagosomes. Eventually, matured phagosomes will fuse to lysosome. Bacteria ended up in lysosome are generally killed, but it is possible that bacteria can be killed during the early steps of phagosome maturation. Two maturation events occurs simultaneously on phagosome before fusing to lysosomes. First is recruitment of LAMP1, which is a protein that recruits Rab7. Second is the formation of multivesicular bodies by the endosomal sorting complex required for transport (ESCRT). These two events appear to be independent, as LAMP1 recruitment can occur in the absence of a major ESCRT component.

Why Use Hrs as a Marker?

Both recruitments of both LAMP1 and ESCRT is controlled by hepatocyte growth factor-regulated tyrosine kinase substrate (Hrs). Because Hrs represents a common point of phagosome maturation before two separable events diverge, and because Hrs is only recruited to phagosome containing fully internalized bacteria, we chose Hrs as a cellular marker for phagocytosis and phagosome maturation.

Methods

To test whether IKE/R3 prevents/delays the recruitment of Hrs, we infected J774, a murine macrophage cell line, with mc$^2$155 or mc$^2$5003 at a MOI 10:1 for 1 h, followed by a 1 h chase in the presence of gentamycin that would eliminate non-phagocytosized bacteria. Infected cells were then fixed, permeabilized, and processed for immunofluorescence staining using a rabbit polyclonal antibody raised against Hrs (Santa Cruz Biotechnology). The antibody had been pre-incubated with a *Mycobacterium* strain to eliminate non-specific binding by the antibody to the bacteria. The anti-Hrs antibody was visualized by an anti-rabbit antibody conjugated with Alexa dye 594. Bacteria were visualized by its ability to autofluorescence at blue color. The percentage of phagosomes that showed Hrs staining were determined from 50 phagosomes in triplicate.

Results

Figure 17:
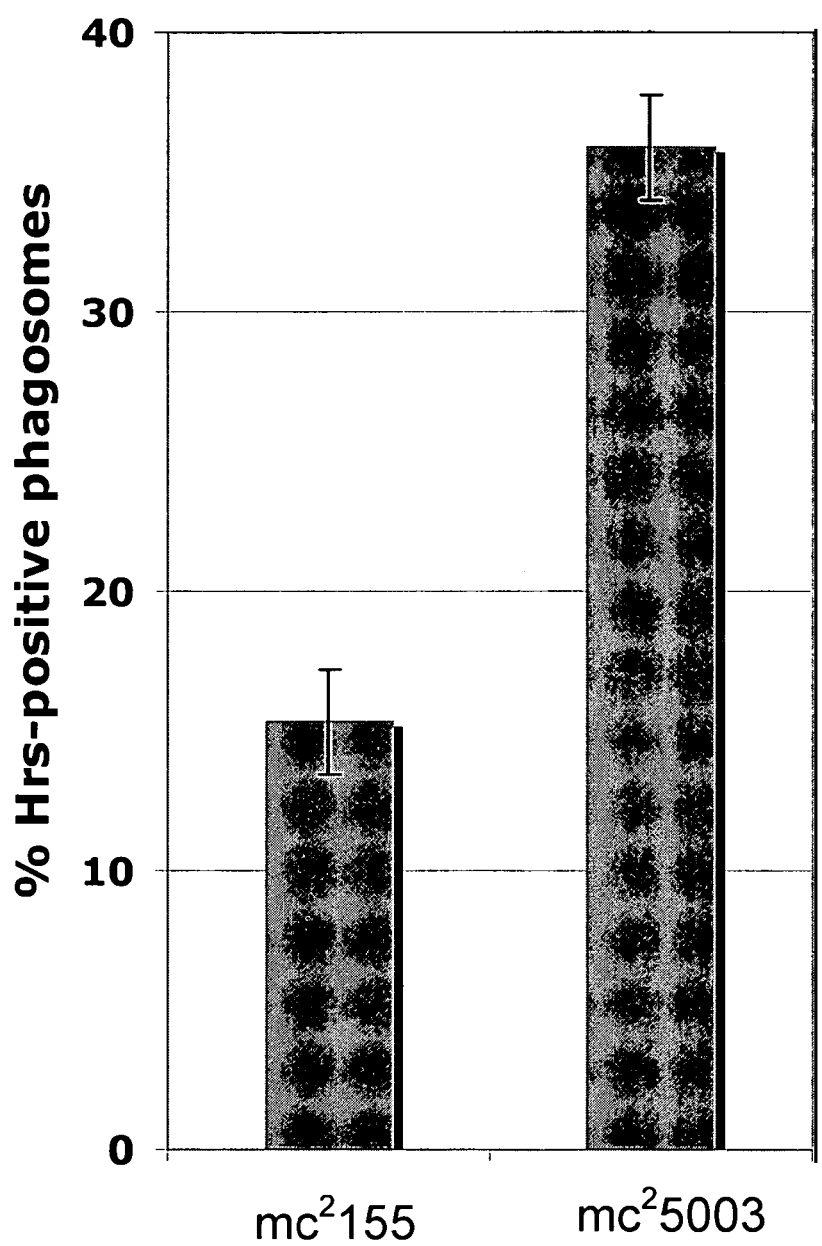
FIG. 17 is a graph showing the ability of two strains of *mycobacterium* to recruit Hrs in infected macrophages.

FIG. 17 demonstrated that R3 mutant mc$^2$5003 clearly had a defect in its ability to prevent Hrs recruitment when compared to the wild-type mc$^2$155.

Discussion

There are three ways that an impairment of Hrs recruitment can lead better killing by macrophages. First is the ability of the phagosome to mature and fuse with lysosome. This possibility is unlikely because mc$^2$155-phagosomes showed the same level of Rab7 recruitment and lysosome co-localization with mc$^2$5003-phagosomes. Secondly, the phagosomes containing *M. smegmatis* without IKE/R3 may undergo more multivesicular bodies formation by ESCRT. The third possibility is that IKE/R3 blocks Hrs recruitment by preventing phagocytosis by macrophages.

REFERENCES

Altare F, Lammas D, Revy P, Jouanguy E, Doffinger R, et al. (1998) Inherited interleukin 12 deficiency in a child with bacille Calmette-Guerin and *Salmonella enteritidis* disseminated infection. J Clin Invest 102: 2035-2040.

Altare F, Ensser A, Breiman A, Reichenbach J, Baghdadi J E, et al. (2001) Interleukin-12 receptor beta1 deficiency in a patient with abdominal tuberculosis. J Infect Dis 184: 231-236.

Andersen-Nissen E, Smith K D, Strobe K L, Barrett S L, Cookson B T, et al. (2005) Evasion of Toll-like receptor 5 by flagellated bacteria. Proc Natl Acad Sci USA 102: 9247-9252.

Bardarov S, Kriakov J, Carriere C, Yu S, Vaamonde C, et al. (1997) Conditionally replicating mycobacteriophages: a system for transposon delivery to *Mycobacterium tuberculosis*. Proc Natl Acad Sci USA 94: 10961-10966.

Bardarov S, Bardarov Jr S, Jr., Pavelka Jr M S, Jr., Sambandamurthy V, Larsen M, et al. (2002) Specialized transduction: an efficient method for generating marked and unmarked targeted gene disruptions in *Mycobacterium tuberculosis, M. bovis* BCG and *M. smegmatis*. Microbiology 148: 3007-3017.

Behr M A, Small P M (1997) Has BCG attenuated to impotence? Nature 389: 133-134.

Campos P E, Suarez P G, Sanchez J, Zavala D, Arevalo J, et al. (2003) Multidrug-resistant *Mycobacterium tuberculosis* in HIV-infected persons, Peru. Emerg Infect Dis 9: 1571-1578.

Chacon-Salinas R, Serafin-Lopez J, Ramos-Payan R, Mendez-Aragon P, Hernandez-Pando R, et al. (2005) Differential pattern of cytokine expression by macrophages infected in vitro with different *Mycobacterium tuberculosis* genotypes. Clin Exp Immunol 140: 443-449.

Coats S R, Reife R A, Bainbridge B W, Pham T T, Darveau R P (2003) *Porphyromonas gingivalis* lipopolysaccharide antagonizes *Escherichia coli* lipopolysaccharide at toll-like receptor 4 in human endothelial cells. Infect Immun 71: 6799-6807.

Cooper A M, Roberts A D, Rhoades E R, Callahan J E, Getzy D M, et al. (1995) The role of interleukin-12 in acquired immunity to *Mycobacterium tuberculosis* infection. Immunology 84: 423-432.

Cooper A M, Magram J, Ferrante J, Orme I M (1997) Interleukin 12 (IL-12) is crucial to the development of protective immunity in mice intravenously infected with *mycobacterium tuberculosis*. J Exp Med 186: 39-45.

Cooper A M, Kipnis A, Turner J, Magram J, Ferrante J, et al. (2002) Mice lacking bioactive IL-12 can generate protective, antigen-specific cellular responses to mycobacterial infection only if the IL-12 p40 subunit is present. J Immunol 168: 1322-1327.

Dao D N, Kremer L, Guerardel Y, Molano A, Jacobs W R, Jr., et al. (2004) *Mycobacterium tuberculosis* lipomannan induces apoptosis and interleukin-12 production in macrophages. Infect Immun 72: 2067-2074.

Darveau R P, Pham T T, Lemley K, Reife R A, Bainbridge B W, et al. (2004) *Porphyromonas gingivalis* lipopolysaccharide contains multiple lipid A species that functionally interact with both toll-like receptors 2 and 4. Infect Immun 72: 5041-5051.

de Jong R, Altare F, Haagen I A, Elferink D G, Boer T, et al. (1998) Severe mycobacterial and *Salmonella* infections in interleukin-12 receptor-deficient patients. Science 280: 1435-1438.

Dinadayala P, Laval F, Raynaud C, Lemassu A, Laneelle M A, et al. (2003) Tracking the putative biosynthetic precursors of oxygenated mycolates of *Mycobacterium tuberculosis*. Structural analysis of fatty acids of a mutant strain deviod of methoxy- and ketomycolates. J Biol Chem 278: 7310-7319.

Dixon D R, Darveau R P (2005) Lipopolysaccharide heterogeneity: innate host responses to bacterial modification of lipid a structure. J Dent Res 84: 584-595.

Doherty T M, Sher A (1998) IL-12 promotes drug-induced clearance of *Mycobacterium avium* infection in mice. J Immunol 160: 5428-5435.

Dubnau E, Chan J, Raynaud C, Mohan V P, Laneelle M A, et al. (2000) Oxygenated mycolic acids are necessary for virulence of *Mycobacterium tuberculosis* in mice. Mol Microbiol 36: 630-637.

Ehlers S, Lehmann J, Mossmann H, Alber G, Holscher C (2005) Interleukin-12p40 mediates transient protection against *Mycobacterium avium* infection in the absence of interleukin-12. Immunobiology 210: 217-227.

Ellingsen E, Morath S, Flo T, Schromm A, Hartung T, et al. (2002) Induction of cytokine production in human T cells and monocytes by highly purified lipoteichoic acid: involvement of Toll-like receptors and CD14. Med Sci Monit 8: BR149-156.

Feng C G, Jankovic D, Kullberg M, Cheever A, Scanga C A, et al. (2005) Maintenance of pulmonary Th1 effector function in chronic tuberculosis requires persistent IL-12 production. J Immunol 174: 4185-4192.

Frieden T R, Sterling T R, Munsiff S S, Watt C J, Dye C (2003) Tuberculosis. Lancet 362: 887-899.

Flynn J L, Chan J (2001) Immunology of tuberculosis. Annu Rev Immunol 19: 93-129.

Flynn J L, Chan J (2003) Immune evasion by *Mycobacterium tuberculosis*: living with the enemy. Curr Opin Immunol 15: 450-455.

Flynn J L (2004) Immunology of tuberculosis and implications in vaccine development. Tuberculosis (Edinb) 84: 93-101.

Flynn J L, Goldstein M M, Triebold K J, Sypek J, Wolf S, et al. (1995) IL-12 increases resistance of BALB/c mice to *Mycobacterium tuberculosis* infection. J Immunol 155: 2515-2524.

Gazzinelli R T, Wysocka M, Hayashi S, Denkers E Y, Hieny S, et al. (1994) Parasite-induced IL-12 stimulates early IFN-gamma synthesis and resistance during acute infection with *Toxoplasma gondii*. J Immunol 153: 2533-2543.

Geisel R E, Sakamoto K, Russell D G, Rhoades E R (2005) In vivo activity of released cell wall lipids of *Mycobacterium bovis bacillus* Calmette-Guerin is due principally to trehalose mycolates. J Immunol 174: 5007-5015.

Gewirtz A T, Yu Y, Krishna U S, Israel D A, Lyons S L, et al. (2004) *Helicobacter pylori* flagellin evades toll-like receptor 5-mediated innate immunity. J Infect Dis 189: 1914-1920.

Gey van Pittius N C et al. (2001) The ESAT-6 gene cluster of *Mycobacterium tuberculosis* and other high G+C Gran-positive bacteria. Genome Biol. 2: research0044.1-0044.18.

Glickman M S, Jacobs W R, Jr. (2001) Microbial pathogenesis of *Mycobacterium tuberculosis*: dawn of a discipline. Cell 104: 477-485.

Grangette C, Nutten S, Palumbo E, Morath S, Hermann C, et al. (2005) Enhanced antiinflammatory capacity of a *Lactobacillus plantarum* mutant synthesizing modified teichoic acids. Proc Natl Acad Sci USA 102: 10321-10326.

Greinert U, Ernst M, Schlaak M, Entzian P (2001) Interleukin-12 as successful adjuvant in tuberculosis treatment. Eur Respir J 17: 1049-1051.

Hajjar A M, Ernst R K, Tsai J H, Wilson C B, Miller S I (2002) Human Toll-like receptor 4 recognizes host-specific LPS modifications. Nat Immunol 3: 354-359.

Hasegawa T, Leblanc R M (2003) Aggregation properties of mycolic acid molecules in monolayer films: a comparative study of compounds from various acid-fast bacterial species. Biochim Biophys Acta 1617: 89-95.

Holscher C (2004) The power of combinatorial immunology: IL-12 and IL-12-related dimeric cytokines in infectious diseases. Med Microbiol Immunol (Berl) 193: 1-17.

Holscher C, Atkinson R A, Arendse B, Brown N, Myburgh E, et al. (2001) A protective and agonistic function of IL-12p40 in mycobacterial infection. J Immunol 167: 6957-6966.

Hickman S P, Chan J, Salgame P (2002) *Mycobacterium tuberculosis* induces differential cytokine production from dendritic cells and macrophages with divergent effects on naive T cell polarization. J Immunol 168: 4636-4642.

Ito K, Fujimori M, Shingu K, Hama Y, Kanai T, et al. (2005) Pulmonary tuberculosis in a patient receiving intensive chemotherapy for metastatic breast cancer. Breast J 11: 87-88.

Iwasaki A, Medzhitov R (2004) Toll-like receptor control of the adaptive immune responses. Nat Immunol 5: 987-995.

Johnson C R, Kitz D, Little J R (1983) A method for the derivation and continuous propagation of cloned murine bone marrow macrophages. J Immunol Methods 65: 319-332.

Jouanguy E, Doffinger R, Dupuis S, Pallier A, Altare F, et al. (1999) IL-12 and IFN-gamma in host defense against mycobacteria and *salmonella* in mice and men. Curr Opin Immunol 11: 346-351.

Jung Y J, LaCourse R, Ryan L, North R J (2002) Virulent but not avirulent *Mycobacterium tuberculosis* can evade the growth inhibitory action of a T helper 1-dependent, nitric oxide Synthase 2-independent defense in mice. J Exp Med 196: 991-998.

Karakousis P C, Bishai W R, Dorman S E (2004) *Mycobacterium tuberculosis* cell envelope lipids and the host immune response. Cell Microbiol 6: 105-116.

Khader S A, Pearl J E, Sakamoto K, Gilmartin L, Bell G K, et al. (2005) IL-23 compensates for the absence of IL-12p70 and is essential for the IL-17 response during tuberculosis but is dispensable for protection and antigen-specific IFN-gamma responses if IL-12p70 is available. J Immunol 175: 788-795.

Khader S A, Partida-Sanchez S, Bell G, Jelley-Gibbs D M, Swain S, et al. (2006) Interleukin 12p40 is required for dendritic cell migration and T cell priming after *Mycobacterium tuberculosis* infection. J Exp Med 203: 1805-1815.

Kim D K L, Sei Won; Yoo, Chul-Gyu; Kim, Young Whan; Han, Sung Koo; Shim, Young-Soo; and Yim, Jae-Joon (2005) Clinical Characteristics and Treatment Responses of Tuberculosis in Patients With Malignancy Receiving Anticancer Chemotherapy. Chest 128: 2218-2222.

Kopp E, Medzhitov R (2003) Recognition of microbial infection by Toll-like receptors. Curr Opin Immunol 15: 396-401.

Manca C, Tsenova L, Barry C E, 3rd, Bergtold A, Freeman S, et al. (1999) *Mycobacterium tuberculosis* CDC1551 induces a more vigorous host response in vivo and in vitro, but is not more virulent than other clinical isolates. J Immunol 162: 6740-6746.

Manetti R, Parronchi P, Giudizi M G, Piccinni M P, Maggi E, et al. (1993) Natural killer cell stimulatory factor (interleukin 12 [IL-12]) induces T helper type 1 (Th1)-specific immune responses and inhibits the development of IL-4-producing Th cells. J Exp Med 177: 1199-1204.

Mastroeni P (2002) Immunity to systemic *Salmonella* infections. Curr Mol Med 2: 393-406.

McDowell M A, Sacks D L (1999) Inhibition of host cell signal transduction by *Leishmania*: observations relevant to the selective impairment of IL-12 responses. Curr Opin Microbiol 2: 438-443.

Miller S I, Ernst R K, Bader M W (2005) LPS, TLR4 and infectious disease diversity. Nat Rev Microbiol 3: 36-46.

Munford R S, Varley A W (2006) Shield as signal: lipopolysaccharides and the evolution of immunity to gram-negative bacteria. PLoS Pathog 2: e67.

Murphy T L, Cleveland M G, Kulesza P, Magram J, Murphy K M (1995) Regulation of interleukin 12 p40 expression through an NF-kappa B half-site. Mol Cell Biol 15: 5258-5267.

Nau G J, Richmond J F, Schlesinger A, Jennings E G, Lander E S, et al. (2002) Human macrophage activation programs induced by bacterial pathogens. Proc Natl Acad Sci USA 99: 1503-1508.

Nigou J, Zelle-Rieser C, Gilleron M, Thurnher M, Puzo G (2001) Mannosylated lipoarabinomannans inhibit IL-12 production by human dendritic cells: evidence for a negative signal delivered through the mannose receptor. J Immunol 166: 7477-7485.

Onyebujoh P, Rook G A (2004) Tuberculosis. Nat. Rev Microbiol 2: 930-932.

Quesniaux V J, Nicolle D M, Torres D, Kremer L, Guerardel Y, et al. (2004) Toll-like receptor 2 (TLR2)-dependent-positive and TLR2-independent-negative regulation of proinflammatory cytokines by mycobacterial lipomannans. J Immunol 172: 4425-4434.

Rachman H, Strong M, Ulrichs T, Grode L, Schuchhardt J, et al. (2006) Unique transcriptome signature of *Mycobacterium tuberculosis* in pulmonary tuberculosis. Infect Immun 74: 1233-1242.

Rao V, Fujiwara N, Porcelli S A, Glickman M S (2005) *Mycobacterium tuberculosis* controls host innate immune activation through cyclopropane modification of a glycolipid effector molecule. J Exp Med 201: 535-543.

Rao V, Gao F, Chen B, Jacobs W R, Jr., Glickman M S (2006) Trans-cyclopropanation of mycolic acids on trehalose dimycolate suppresses *Mycobacterium tuberculosis*-induced inflammation and virulence. J Clin Invest 116: 1660-1667.

Reed M B, Domenech P, Manca C, Su H, Barczak A K, et al. (2004) A glycolipid of hypervirulent tuberculosis strains that inhibits the innate immune response. Nature 431: 84-87.

Reiner S L, Zheng S, Wang Z E, Stowring L, Locksley R M (1994) *Leishmania* promastigotes evade interleukin 12 (IL-12) induction by macrophages and stimulate a broad range of cytokines from CD4+ T cells during initiation of infection. J Exp Med 179: 447-456.

Rhoades E, Hsu F, Torrelles J B, Turk J, Chatterjee D, et al. (2003) Identification and macrophage-activating activity of glycolipids released from intracellular *Mycobacterium bovis* BCG. Mol Microbiol 48: 875-888.

Rubin E J, Akerley B J, Novik V N, Lampe D J, Husson R N, et al. (1999) In vivo transposition of mariner-based elements in enteric bacteria and mycobacteria. Proc Natl Acad Sci USA 96: 1645-1650.

Sassetti C M, Boyd D H, Rubin E J (2001) Comprehensive identification of conditionally essential genes in mycobacteria. Proc Natl Acad Sci USA 98: 12712-12717.

Stead W W, Dutt A K (1991) Tuberculosis in elderly persons. Annu Rev Med 42: 267-276.

Takayama K, Wang C, Besra G S (2005) Pathway to synthesis and processing of mycolic acids in *Mycobacterium tuberculosis*. Clin Microbiol Rev 18: 81-101.

Takeuchi O, Hoshino K, Kawai T, Sanjo H, Takada H, et al. (1999) Differential roles of TLR2 and TLR4 in recognition of gram-negative and gram-positive bacterial cell wall components. Immunity 11: 443-451.

Trinchieri G (2003) Interleukin-12 and the regulation of innate resistance and adaptive immunity. Nat Rev Immunol 3: 133-146.

Tullius M V, Harth G, Horwitz M A (2001) High extracellular levels of *Mycobacterium tuberculosis* glutamine synthetase and superoxide dismutase in actively growing cultures are due to high expression and extracellular stability rather than to a protein-specific export mechanism. Infect Immun 69: 6348-6363.

Van Boxtel R M, Lambrecht R S, Collins M T (1990) Effects of colonial morphology and tween 80 on antimicrobial susceptibility of *Mycobacterium paratuberculosis*. Antimicrob Agents Chemother 34: 2300-2303.

Villeneuve M, Kawai M, Kanashima H, Watanabe M, Minnikin D E, et al. (2005) Temperature dependence of the Langmuir monolayer packing of mycolic acids from *Mycobacterium tuberculosis*. Biochim Biophys Acta 1715: 71-80.

Yoshida A, Koide Y (1997) Arabinofuranosyl-terminated and mannosylated lipoarabinomannans from *Mycobacterium tuberculosis* induce different levels of interleukin-12 expression in murine macrophages. Infect Immun 65: 1953-1955.

Yuan Y, Zhu Y, Crane D D, Barry C E, 3rd (1998) The effect of oxygenated mycolic acid composition on cell wall function and macrophage growth in *Mycobacterium tuberculosis*. Mol Microbiol 29: 1449-1458.

Zhan Y, Cheers C (1998) Control of IL-12 and IFN-gamma production in response to live or dead bacteria by TNF and other factors. J Immunol 161: 1447-1453.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

APPENDIX 1

Annotation of genes Ms0615-0626 from nc_008596

| | |
|---|---|
| gene | 691998 ... 693767 |
| | /locus_tag = "MSMEG_0615" |
| | /db_xref = "GeneID: 4535974" |
| CDS | 691998 ... 693767 |
| | /locus_tag = "MSMEG_0615" |
| | /note = "identified by match to protein family HMM PF00004" |
| | /codon_start = 1 |
| | /transl_table = 11 |
| | /product = "ATPase, AAA family protein" |
| | /protein_id = "YP_885026.1" |
| | /db_xref = "GI: 118467798" |
| | /db_xref = "GeneID: 4535974" |
| gene | 693764 ... 695320 |
| | /locus_tag = "MSMEG_0616" |
| | /db_xref = "GeneID: 4531181" |
| CDS | 693764 ... 695320 |
| | /locus_tag = "MSMEG_0616" |
| | /note = "identified by match to protein family HMM PF05108" |
| | /codon_start = 1 |
| | /transl_table = 11 |
| | /product = "hypothetical protein" |
| | /protein_id = "YP_885027.1" |
| | /db_xref = "GI: 118473477" |
| | /db_xref = "GeneID: 4531181" |
| gene | 695317 ... 699294 |
| | /locus_tag = "MSMEG_0617" |
| | /db_xref = "GeneID: 4537422" |
| CDS | 695317 ... 699294 |
| | /locus_tag = "MSMEG_0617" |
| | /note = "identified by match to protein family HMM PF01580" |
| | /codon_start = 1 |
| | /transl_table = 11 |
| | /product = "ftsk/spoiiie family protein" |
| | /protein_id = "YP_885028.1" |
| | /db_xref = "GI: 118468237" |
| | /db_xref = "GeneID: 4537422" |
| gene | 699291 ... 699602 |
| | /locus_tag = "MSMEG_0618" |
| | /db_xref = "GeneID: 4531916" |
| CDS | 699291 ... 699602 |
| | /locus_tag = "MSMEG_0618" |
| | /note = "identified by match to protein family HMM PF00934" |
| | /codon_start = 1 |
| | /transl_table = 11 |
| | /product = "pe family protein" |
| | /protein_id = "YP_885029.1" |
| | /db_xref = "GI: 118470806" |
| | /db_xref = "GeneID: 4531916" |

APPENDIX 1-continued

Annotation of genes Ms0615-0626 from nc_008596

| | |
|---|---|
| gene | 699604 ... 701175 |
| | /locus_tag = "MSMEG_0619" |
| | /db_xref = "GeneID: 4534257" |
| CDS | 699604 ... 701175 |
| | /locus_tag = "MSMEG_0619" |
| | /note = "identified by match to protein family HMM PF00823" |
| | /codon_start = 1 |
| | /transl_table = 11 |
| | /product = "ppe family protein" |
| | /protein_id = "YP_885030.1" |
| | /db_xref = "GI: 118468729" |
| | /db_xref = "GeneID: 4534257" |
| gene | 701225 ... 701518 |
| | /locus_tag = "MSMEG_0620" |
| | /db_xref = "GeneID: 4534464" |
| CDS | 701225 ... 701518 |
| | /locus_tag = "MSMEG_0620" |
| | /codon_start = 1 |
| | /transl_table = 11 |
| | /product = "pe family protein" |
| | /protein_id = "YP_885031.1" |
| | /db_xref = "GI: 118469490" |
| | /db_xref = "GeneID: 4534464" |
| gene | 701553 ... 701840 |
| | /locus_tag = "MSMEG_0621" |
| | /db_xref = "GeneID: 4532995" |
| CDS | 701553 ... 701840 |
| | /locus_tag = "MSMEG_0621" |
| | /codon_start = 1 |
| | /transl_table = 11 |
| | /product = "low molecular weight protein antigen 7" |
| | /protein_id = "YP_885032.1" |
| | /db_xref = "GI: 118470541" |
| | /db_xref = "GeneID: 4532995" |
| gene | 701853 ... 702734 |
| | /locus_tag = "MSMEG_0622" |
| | /db_xref = "GeneID: 4531925" |
| CDS | 701853 ... 702734 |
| | /locus_tag = "MSMEG_0622" |
| | /codon_start = 1 |
| | /transl_table = 11 |
| | /product = "putative DNA-binding protein" |
| | /protein_id = "YP_885033.1" |
| | /db_xref = "GI: 118470815" |
| | /db_xref = "GeneID: 4531925" |
| gene | 702737 ... 704164 |
| | /gene = "snm" |
| | /locus_tag = "MSMEG_0623" |
| | /db_xref = "GeneID: 4536194" |
| CDS | 702737 ... 704164 |
| | /gene = "snm" |
| | /locus_tag = "MSMEG_0623" |
| | /note = "identified by match to protein family HMM PF04600; match to protein family HMM TIGR02958" |
| | /codon_start = 1 |
| | /transl_table = 11 |
| | /product = "secretion protein Snm4" |
| | /protein_id = "YP_885034.1" |
| | /db_xref = "GI: 118471932" |
| | /db_xref = "GeneID: 4536194" |
| gene | 704172 ... 705551 |
| | /locus_tag = "MSMEG_0624" |
| | /db_xref = "GeneID: 4535326" |
| CDS | 704172 ... 705551 |
| | /locus_tag = "MSMEG_0624" |
| | /note = "identified by match to protein family HMM PF00082" |
| | /codon_start = 1 |
| | /transl_table = 11 |
| | /product = "subtilase family protein" |
| | /protein_id = "YP_885035.1" |
| | /db_xref = "GI: 118469114" |
| | /db_xref = "GeneID: 4535326" |
| gene | 705548 ... 706477 |
| | /locus_tag = "MSMEG_0626" |
| | /db_xref = "GeneID: 4536438" |

APPENDIX 1-continued

Annotation of genes Ms0615-0626 from nc_008596

| | |
|---|---|
| CDS | 705548 ... 706477<br>/locus_tag = "MSMEG_0626"<br>/codon_start = 1<br>/transl_table = 11<br>/product = "hypothetical protein"<br>/protein_id = "YP_885036.1"<br>/db_xref = "GI: 118471713"<br>/db_xref = "GeneID: 4536438" |
| gene | complement(706433 ... 707632)<br>/locus_tag = "MSMEG_0625"<br>/db_xref = "GeneID: 4533486" |
| CDS | complement(706433 ... 707632)<br>/locus_tag = "MSMEG_0625"<br>/codon_start = 1<br>/transl_table = 11<br>/product = "hypothetical protein"<br>/protein_id = "YP_885037.1"<br>/db_xref = "GI: 118470994"<br>/db_xref = "GeneID: 4533486" |

APPENDIX 2

SEQ ID NOs

SEQ ID NO: 1 *Mycobacterium tuberculosis* roc-1 (=mma4) gene 5025-5930 of GenBank U66108

```
5025 atgacg agaatggccg 5041 agaaaccgat tagcccaacc aagcacgga cacgcttcga agacatccaa gcgcactacg 5101 acgtctccga tgatttcttc gccctgttcc aggacccgac ccgaacttac agctgtgcct 5161 acttcgagcc accggagctc acgctcgaag aagcccaata cgccaaggtc gacctcaacc 5221 tggacaagct ggacctcaag ccgggcatga cgctgctgga cattgggtgc ggttggggca 5281 ccaccatgag gcgcgccgtc gagcggttcg acgttaacgt catcggcctg acgttgtcca 5341 agaaccagct cgcccgctgc gagcaagtgc tggcttcgat cgacaccaac cgctcacgtc 5401 aagtgctgct gcaaggctgg gaggatttcg ccgaacccg cgaccggatt gtgtcgatcg 5461 aagccttcga gcacttcggg cacgagaact acgacgactt cttcaagcgg tgtttcaaca 5521 tcatgcccgc cgacggccgg atgaccgtcc agagcagcgt cagctaccac ccctacgaga 5581 tggcggcccg cggtaagaag ctgagcttcg agacggcgcg tttcatcaag ttcatcgtca 5641 ccgagatatt tcccggcggc cgcctgccgt ccaccgagat gatggtcgaa cacggcgaga 5701 aggccggttt caccgtcccg gagccgctct cgttgcgccc gcattacatc aagacgctgc 5761 ggatctgggg ggacacgctg cagtccaata aggacaaggc catcgaggtc acctccgaag 5821 aggtctacaa ccgctacatg aagtatttgc gtggctgcga gcactacttc accgacgaga 5881 tgctcgactg cagcctggtg acctacctca gcccgggtgc cgcggcctaa
```

SEQ ID NO: 2 *Mycobacterium tuberculosis* roc-1 (=mma4) amino acid sequence, from Genbank U66108

MTRMAEKPISPTKTRTRFEDIQAHYDVSDDFFALFQDPIRTYSCAYFEPPELTLEEAQYAKVDLNLDK

LDLKPGMTLLDIGCGWGTTMRRAVERFDVNVIGLTLSKNQLARCEQVLASIDTNRSRQVLLQGWED

FAEPVDRIVSIEAFEHFGHENYDDFFKRCFNIMPADGRMTVQSSVSYHPYEMAARGKKLSFETARFIK

FIVTEIFPGGRLPSTEMMVEHGEKAGFTVPEPLSLRPHYIKTLRIWGDTLQSNKDKAIEVTSEEVYNRY

MKYLRGCEHYFTDEMLDCSLVTYLKPGAAA

What is claimed is:

1. A recombinant *mycobacterium* comprising a deletion of a gene of a region 3 ESAT-6-like gene cluster, wherein the *mycobacterium* is not an *M. tuberculosis*.

2. The *mycobacterium* of claim 1, wherein the region 3 ESAT-6-like gene cluster is deleted.

3. The *mycobacterium* of claim 1, wherein the deletion comprises at least genes analogous to Ms0615-Ms0626 as identified in the GenBank *M. smegmatis* genome sequence nc_008596.

4. The *mycobacterium* of claim 1, wherein the *mycobacterium* is *M. smegmatis, M. bovis, M. avium, M. phlei, M. fortuitum, M. lufu, M. paratuberculosis, M. habana, M. scrofulacium, M. intracellulare,* or *M. kansasii*.

5. The *mycobacterium* of claim 1, wherein the *mycobacterium* is an *M. smegmatis*.

6. The *mycobacterium* of claim 1, genetically complemented with Region 3 from an *M. tuberculosis*.

7. The *mycobacterium* of claim 6, wherein the *mycobacterium* is genetically complemented with genes comprising RV0283-RV0291 from *M. tuberculosis*.

8. The *mycobacterium* of claim 1, further comprising a recombinant gene operably linked to a promoter that directs expression of the gene when the *mycobacterium* infects a mammalian cell.

9. The *mycobacterium* of claim 8, wherein the gene encodes an antigen of a mammalian pathogen.

10. A method of inducing an immune response in a mammal, the method comprising inoculating the mammal with the *mycobacterium* of 54.

11. A method of inducing an immune response in a mammal, the method comprising inoculating the mammal with the *mycobacterium* of 60.

12. A method of making the recombinant *mycobacterium* of claim 1, the method comprising deleting a gene of a region 3 ESAT-6-like gene cluster, wherein the *mycobacterium* is not an *M. tuberculosis*.

13. A method of making the recombinant *mycobacterium* of claim 6, the method comprising deleting a gene of a region 3 ESAT-6-like gene cluster in the *mycobacterium*, wherein the *mycobacterium* is not an *M. tuberculosis*, and genetically complementing the *mycobacterium* with an *M. tuberculosis* region 3 ESAT-6-like gene cluster.

14. A recombinant *mycobacterium* comprising a mutation in a roc-1 gene, wherein the mutation increases the ability of the *mycobacterium* to induce IL-12 and/or TNF-α production in a mammalian macrophage infected by the *mycobacterium*, and wherein the *mycobacterium* is not a virulent *Mycobacterium tuberculosis*.

15. The *mycobacterium* of claim 14, wherein the mutation is a deletion.

16. The *mycobacterium* of claim 15 wherein the deletion is a deletion of the entire roc-1 gene (Δroc-1).

17. The *mycobacterium* of claim 14, wherein the *mycobacterium* is *M. smegmatis, M. bovis, M. avium, M. phlei, M. fortuitum, M. lufu, M. paratuberculosis, M. habana, M. scrofulacium, M. intracellulare,* an attenuated or avirulent *M. tuberculosis* or *M. kansasii*.

18. The *mycobacterium* of claim 17, wherein the *mycobacterium* is *M. bovis* BCG.

19. The *mycobacterium* of claim 17, wherein the *mycobacterium* is an *M. tuberculosis* H37ra.

20. The *mycobacterium* of claim 17, wherein the *mycobacterium* is an *M. tuberculosis* further comprising a deletion in a second gene, wherein the second gene by itself attenuates the virulence of the *M. tuberculosis*.

21. A method of making the recombinant *mycobacterium* of claim 14, the method comprising genetically creating a mutation in a roc-1 gene, wherein the mutation increases the ability of the *mycobacterium* to induce IL-12 and/or TNF-α production in a mammalian macrophage infected by the *mycobacterium*, and wherein the *mycobacterium* is not a virulent *Mycobacterium tuberculosis*.

22. A method of inhibiting IL-12 production in a mammal, the method comprising treating the mammal with (i) purified trehalose 6'-6' dimycolates from a virulent *Mycobacterium tuberculosis*, or (ii) a purified keto mycolate esterified to trehalose, or (iii) a purified methoxy mycolate esterified to trehalose, or (iv) a purified keto mycolate esterified to trehalose and a purified methoxy mycolate esterified to trehalose.

23. A method of stimulating IL-12 production in a mammal, the method comprising treating the mammal with (i) purified trehalose 6'-6' dimycolates from *Mycobacterium tuberculosis* Δroc-1, or (ii) purified α-mycolate, or (iii) purified epoxy mycolate esterified to trehalose.

24. A vaccine or vaccine adjuvant comprising (i) purified trehalose 6'-6' dimycolates from *Mycobacterium tuberculosis* Δroc-1, (ii) purified α-mycolate, or (iii) purified epoxy mycolate esterified to trehalose.

25. The method of claim 10, wherein the mammal is a mouse.

* * * * *

UNITED STATES PATENT AND TRADEMARK OFFICE
CERTIFICATE OF CORRECTION

PATENT NO. : 8,591,918 B2  
APPLICATION NO. : 12/450193  
DATED : November 26, 2013  
INVENTOR(S) : William R. Jacobs, Jr. et al.

It is certified that error appears in the above-identified patent and that said Letters Patent is hereby corrected as shown below:

Column 1, lines 14-19, should read:

-- STATEMENT OF GOVERNMENT SUPPORT

This invention was made with government support under grant numbers AI063537, AI026170 and AI052816 awarded by the National Institutes of Health. The government has certain rights in the invention. --

Signed and Sealed this
Tenth Day of November, 2015

Michelle K. Lee
*Director of the United States Patent and Trademark Office*

SEQUENCE LISTING

<160> NUMBER OF SEQ ID NOS: 12

<210> SEQ ID NO 1
<211> LENGTH: 906
<212> TYPE: DNA
<213> ORGANISM: Mycobacterium tuberculosis

<400> SEQUENCE: 1

```
atgacgagaa tggccgagaa accgattagc ccaaccaaga cacggacacg cttcgaagac    60
atccaagcgc actacgacgt ctccgatgat ttcttcgccc tgttccagga cccgacccga   120
acttacagct gtgcctactt cgagccaccg gagctcacgc tcgaagaagc caatacgcc    180
aaggtcgacc tcaacctgga caagctggac ctcaagccgg gcatgacgct gctggacatt   240
gggtgcggtt ggggcaccac catgaggcgc gccgtcgagc ggttcgacgt taacgtcatc   300
ggcctgacgt tgtccaagaa ccagctcgcc cgctgcgagc aagtgctggc ttcgatcgac   360
accaaccgct cacgtcaagt gctgctgcaa ggctgggagg atttcgccga cccgtcgac   420
cggattgtgt cgatcgaagc cttcgagcac ttcgggcacg agaactacga cgacttcttc   480
aagcggtgtt tcaacatcat gcccgccgac ggccggatga ccgtccagag cagcgtcagc   540
taccaccct acgagatggc ggcccgcggt aagaagctga gcttcgagac ggcgcgtttc   600
atcaagttca tcgtcaccga gatatttccc ggcggccgcc tgccgtccac cgagatgatg   660
gtcgaacacg gcgagaaggc cggtttcacc gtcccggagc cgctctcgtt gcgcccgcat   720
tacatcaaga cgctgcggat ctgggggac acgctgcagt ccaataagga caaggccatc   780
gaggtcaccg ccgaagaggt ctacaaccgc tacatgaagt atttgcgtgg ctgcgagcac   840
tacttcaccg acgagatgct cgactgcagc ctggtgacct acctcaagcc gggtgccgcg   900
gcctaa                                                              906
```

<210> SEQ ID NO 2
<211> LENGTH: 301
<212> TYPE: PRT
<213> ORGANISM: Mycobacterium tuberculosis

<400> SEQUENCE: 2

```
Met Thr Arg Met Ala Glu Lys Pro Ile Ser Pro Thr Lys Thr Arg Thr
1               5                   10                  15

Arg Phe Glu Asp Ile Gln Ala His Tyr Asp Val Ser Asp Asp Phe Phe
                20                  25                  30

Ala Leu Phe Gln Asp Pro Thr Arg Thr Tyr Ser Cys Ala Tyr Phe Glu
            35                  40                  45

Pro Pro Glu Leu Thr Leu Glu Glu Ala Gln Tyr Ala Lys Val Asp Leu
        50                  55                  60

Asn Leu Asp Lys Leu Asp Leu Lys Pro Gly Met Thr Leu Leu Asp Ile
65                  70                  75                  80

Gly Cys Gly Trp Gly Thr Thr Met Arg Arg Ala Val Glu Arg Phe Asp
                85                  90                  95

Val Asn Val Ile Gly Leu Thr Leu Ser Lys Asn Gln Leu Ala Arg Cys
                100                 105                 110

Glu Gln Val Leu Ala Ser Ile Asp Thr Asn Arg Ser Arg Gln Val Leu
            115                 120                 125

Leu Gln Gly Trp Glu Asp Phe Ala Glu Pro Val Asp Arg Ile Val Ser
        130                 135                 140

Ile Glu Ala Phe Glu His Phe Gly His Glu Asn Tyr Asp Asp Phe Phe
```

```
                145                 150                 155                 160
Lys Arg Cys Phe Asn Ile Met Pro Ala Asp Gly Arg Met Thr Val Gln
                    165                 170                 175

Ser Ser Val Ser Tyr His Pro Tyr Glu Met Ala Ala Arg Gly Lys Lys
                180                 185                 190

Leu Ser Phe Glu Thr Ala Arg Phe Ile Lys Phe Ile Val Thr Glu Ile
            195                 200                 205

Phe Pro Gly Gly Arg Leu Pro Ser Thr Glu Met Met Val Glu His Gly
        210                 215                 220

Glu Lys Ala Gly Phe Thr Val Pro Glu Pro Leu Ser Leu Arg Pro His
225                 230                 235                 240

Tyr Ile Lys Thr Leu Arg Ile Trp Gly Asp Thr Leu Gln Ser Asn Lys
                245                 250                 255

Asp Lys Ala Ile Glu Val Thr Ser Glu Val Tyr Asn Arg Tyr Met
            260                 265                 270

Lys Tyr Leu Arg Gly Cys Glu His Tyr Phe Thr Asp Glu Met Leu Asp
        275                 280                 285

Cys Ser Leu Val Thr Tyr Leu Lys Pro Gly Ala Ala Ala
    290                 295                 300

<210> SEQ ID NO 3
<211> LENGTH: 21
<212> TYPE: DNA
<213> ORGANISM: artificial sequence
<220> FEATURE:
<223> OTHER INFORMATION: upstream primer for amplification of positions
      -800 to +55 relative to the transcription start of IL-12p40
      promoter

<400> SEQUENCE: 3
acaggattgc acacctcttt g                                              21

<210> SEQ ID NO 4
<211> LENGTH: 16
<212> TYPE: DNA
<213> ORGANISM: artificial sequence
<220> FEATURE:
<223> OTHER INFORMATION: downstream primer for amplification of
      positions -800 to +55 relative to transcription start of IL-12p40
      promoter

<400> SEQUENCE: 4
ttgctttgct gcgagc                                                    16

<210> SEQ ID NO 5
<211> LENGTH: 44
<212> TYPE: DNA
<213> ORGANISM: artificial sequence
<220> FEATURE:
<223> OTHER INFORMATION: 0643cRL primer directed to M. tuberculosis gene

<400> SEQUENCE: 5
ttttttttcc atagattggt cactcgatca ccggcttgca cgta                     44

<210> SEQ ID NO 6
<211> LENGTH: 44
<212> TYPE: DNA
<213> ORGANISM: artificial sequence
<220> FEATURE:
<223> OTHER INFORMATION: 0643cRR primer directed to M. tuberculosis gene

<400> SEQUENCE: 6
ttttttttcc atcttttggg gagacgtcgt agtgcgcttg gatg                     44
```

```
<210> SEQ ID NO 7
<211> LENGTH: 43
<212> TYPE: DNA
<213> ORGANISM: artificial sequence
<220> FEATURE:
<223> OTHER INFORMATION: 0643cLL primer directed to M. tuberculosis gene

<400> SEQUENCE: 7
tttttttacc ataaattggg gaacagtcgg cgaagacggg ttt                 43

<210> SEQ ID NO 8
<211> LENGTH: 44
<212> TYPE: DNA
<213> ORGANISM: artificial sequence
<220> FEATURE:
<223> OTHER INFORMATION: 0643cLR primer directed to M. tuberculosis gene

<400> SEQUENCE: 8 tttttttttcc atttcttggt gaagttggcc cagtcgctca gcag                44

<210> SEQ ID NO 9
<211> LENGTH: 41
<212> TYPE: DNA
<213> ORGANISM: artificial sequence
<220> FEATURE:
<223> OTHER INFORMATION: 0642cRL primer directed to M. tuberculosis gene

<400> SEQUENCE: 9 tttttttttcc atagattggt tcgagacggc gcgtttcatc a                   41

<210> SEQ ID NO 10
<211> LENGTH: 41
<212> TYPE: DNA
<213> ORGANISM: artificial sequence
<220> FEATURE:
<223> OTHER INFORMATION: primer directed to M. tuberculosis gene

<400> SEQUENCE: 10 tttttttttcc atcttttggc gacccgcgta aggcagacca g                   41

<210> SEQ ID NO 11
<211> LENGTH: 45
<212> TYPE: DNA
<213> ORGANISM: artificial sequence
<220> FEATURE:
<223> OTHER INFORMATION: primer directed to M. tuberculosis gene

<400> SEQUENCE: 11
tttttttacc ataaattgga gcactcgatc accggcttgc acgta                45

<210> SEQ ID NO 12
<211> LENGTH: 44
<212> TYPE: DNA
<213> ORGANISM: artificial sequence
<220> FEATURE:
<223> OTHER INFORMATION: 0642cLR primer directed to M. tuberculosis gene

<400> SEQUENCE: 12 tttttttttcc atttcatggt ccaaccgcac ccaatgtcca gcag                44
```